(12) United States Patent
Jiang et al.

(10) Patent No.: US 11,103,601 B2
(45) Date of Patent: Aug. 31, 2021

(54) LYMPH TARGETING NUCLEAR MAGNETIC CONTRAST AGENT USING BROWN ALGAE POLYSACCHARIDE AS CARRIER AND PREPARATION METHOD AND USE THEREOF

(71) Applicant: OCEAN UNIVERSITY OF CHINA, Shandong (CN)

(72) Inventors: Tao Jiang, Shandong (CN); Shengbiao Wan, Shandong (CN); Wei Shang, Shandong (CN); Nan Zhang, Shandong (CN); Mingliang Zhao, Shandong (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 15/760,650

(22) PCT Filed: Aug. 18, 2016

(86) PCT No.: PCT/CN2016/095826
§ 371 (c)(1),
(2) Date: Mar. 16, 2018

(87) PCT Pub. No.: WO2017/045509
PCT Pub. Date: Mar. 23, 2017

(65) Prior Publication Data
US 2018/0272010 A1    Sep. 27, 2018

(30) Foreign Application Priority Data

Sep. 16, 2015  (CN) .......................... 201510588832.4

(51) Int. Cl.
*A61B 5/055* (2006.01)
*A61K 49/12* (2006.01)
*A61K 49/10* (2006.01)

(52) U.S. Cl.
CPC ............ *A61K 49/12* (2013.01); *A61K 49/128* (2013.01); *A61K 49/101* (2013.01)

(58) Field of Classification Search
None
See application file for complete search history.

(56) References Cited

U.S. PATENT DOCUMENTS

| 5,336,506 A * | 8/1994 | Josephson | .......... | A61K 49/0442 424/488 |
| 2012/0093725 A1 * | 4/2012 | Michel | ............... | A61K 49/0002 424/1.73 |

FOREIGN PATENT DOCUMENTS

| CN | 1943791 A | 4/2007 |
| CN | 101325978 A | 12/2008 |
| CN | 101433726 | 5/2009 |
| CN | 101619106 | 1/2010 |
| CN | 101637612 | 2/2010 |
| CN | 101745124 A | 6/2010 |
| CN | 101833253 A | 9/2010 |
| CN | 101899270 A | 12/2010 |
| CN | 101862461 B | 1/2012 |
| CN | 102504603 A | 6/2012 |
| CN | 101619106 A | 7/2012 |
| CN | 103254375 A | 8/2013 |
| CN | 103665726 A | 3/2014 |
| CN | 105148291 A | 12/2015 |
| CN | 105343900 A | 2/2016 |
| CN | 106750057 A | 5/2017 |

OTHER PUBLICATIONS

Zengjiang, Wei; "Preparation and Research of Biotic Super-Hydrophobic Surface"; Shandong Institute of Light Industry, Jinan, China; May 2010.

Zhu Shenmin, Zhang Bin, Li Ming and Yan Deyue; "Synthesis of Poly(styrene-b-methyl methacrylate) block copolymer by ATRP catalyzed by FeCl2/iminodiacetic acid"; China Synthetic Rubber Industry, Jul. 15, 2000, 23(4), 243.

* cited by examiner

*Primary Examiner* — Michael G. Hartley
*Assistant Examiner* — Melissa J Perreira
(74) *Attorney, Agent, or Firm* — Adam Warwick Bell; Matthew Rupert Kaser; Joseph Curtis Edmondson

(57) ABSTRACT

Disclosed is a lymph targeting nuclear magnetic contrast agent using a brown algae polysaccharide as a carrier, and a preparation method and a use thereof. A macromolecular contrast agent with good water solubility was prepared by using the brown algae polysaccharide as the carrier, using mannose or mannose derivatives as a mannose receptor (MBP) recognition group, and using a paramagnetic metal ion chelate as a nuclear magnetic resonance imaging group. The binding capacity of lymphoid tissue was improved. The mannose or mannose derivative group introduced into the synthesized contrast agent molecule achieves the goal of binding to the enriched mannose receptors in the lymphoid tissues. At the same time, after the contrast agent is injected subcutaneously, both lymph vessels and lymph nodes were clearly visualized under MRI scanning. The intensification rate and enhancement time of the lymph node signal at one side of the animal body injected with the contrast agent was significantly enhanced, so as to achieve a clear mapping and precise positioning of the lymph nodes and the lymph vessels. It is of great significance for the detection and diagnosis of lymph system diseases.

12 Claims, 11 Drawing Sheets

LYMPH TARGETING NUCLEAR MAGNETIC CONTRAST AGENT USING BROWN ALGAE POLYSACCHARIDE AS CARRIER AND PREPARATION METHOD AND USE THEREOF

TECHNICAL FIELD OF THE PRESENT INVENTION

The present invention relates to a medical contrast agent, in particular to a lymph targeted contrast agent with a fucoidan as a carrier, a preparation method thereof and an application thereof.

TECHNICAL BACKGROUND OF THE PRESENT INVENTION

A lymphatic system is a network structure consisting of lymph nodes and lymph vessels, is roughly parallel to capillaries and veins and distributed throughout all parts of the body. As an important part of the body's immune system, the lymphatic system plays a key role in the spread of germs and cancer metastasis. Studies have shown that when breast cancer cells and melanoma cells metastasize, sentinel lymph nodes (SLNs) have the most possibility to first find metastasizing cancer cells. The metastasizing cancer cells take SLNs as a reservoir, spread along the lymphatic vessels, invade the lymph nodes at all levels, and ultimately complete the spread of the cancer cells throughout the body. Therefore, lymphatic system angiography, as a means of medical testing, is of great significance in the prevention, the diagnosis, the evaluation and definition of the various stages and the treatment of cancer metastasis.

Magnetic Resonance Imaging (MRI) technology plays a decisive role in the medical development diagnosis and treatment. MRI contrast agent may enhance the signal contrast between normal tissues and diseased tissues and improve the sharpness of an image and disease detection rate; with the rapid rise and development of medical NMR technology in recent ten years, the development of the contrast agent with targeting, solubility, safety and stability has become a trend.

In recent years, lymphatic magnetic resonance imaging (MRI) has been widely used as a noninvasive technique with high resolution. Due to the unique open structure of the lymphatic system and the one-way flow of lymphatic fluid, it is always a hot topic in medical imaging research to develop a highly targeted lymphatic contrast agent of the lymphatic system so as to obtain a lymphatic system MRI image with high sensitivity and sharpness. At present, the commonly used clinical contrast agent is mainly small molecules of the contrast agent containing gadolinium (such as Magnevist), the contrast agent may be used for enhancing and developing blood vessels but may not specifically develop the sentinel lymph nodes and the lymphatic vessels; another tissue-specific MRI contrast agent used clinically is an ultra-small superparamagnetic iron oxide nanoparticles (USPIO) feridex, which is mainly used for magnetic resonance imaging for liver and spleen; therefore, so far, there is no a clinical drug which is specific for the lymphatic system and the sentinel lymph nodes. A series of research for the new lymphatic targeted MR contrast agent may improve the drawing quality of the lymphatic system and provide great help for the localization of the lymph nodes, the staging evaluation of a metastatic tumor, and the functional diagnosis of lymphatic channels such as lymphedema.

Over the past 10 years, the MRI contrast agent on liver, tumor, brain and other special parts has made great progress, for example, CN101637612 discloses a lipid-gadolinium complex used as a respiratory magnetic resonance spray contrast agent, CN101433726 discloses a gadolinium magnetic resonance imaging agent with a carbon nanotube as a carrier, CN1943791A discloses a prepared macromolecular contrast agent for tumor targeting with a dendrimer macromolecule as a carrier with 1,4,7,10-tetraazacyclododecane as a nuclear for connecting a paramagnetic metal.

In the study of an imaging mechanism of a lymphatic targeted contrast, Application No. 201010023087.6 discloses a gadolinium magnetic resonance contrast agent encapsulated in a silica nano-sphere, due to the size range of the contrast agent is 50-200 nm, the contrast agent may be passively absorbed by capillary lymphatic vessels without penetrating the capillaries. In addition, the study of the lymphatic targeted contrast agent with polysaccharide as a carrier is also an important aspect of the development of such contrast agent, for example, chelates (Yan Guoping, polysaccharide macromolecular paramagnetic metal complexes and the synthesis thereof, Chinese Patent Application No. 200910063629.X, Jiang Tao Et al., Preparation of lymphatic system targeted contrast agent and animal experiments thereof. Chinese Science: Chemistry, 2011 (11): pp. 1712-1718) containing gadolinium in covalent connection with dextran (i.e., glucosan) as a carrier, the reason why macromolecular MRI contrast agents are not used clinically is mainly because silica nano-spheres and dextran (glucosan) do not specifically bind lymphocytes and macrophages, which is based on the fact that epithelial cell fissures of lymphatic capillaries are larger than those of the capillaries, after subcutaneous injection, through the difference of the osmotic pressure inside and outside the lymphatic vessels, macromolecules that passively contain gadolinium chelate are pressed into the lymphatic vessels, which does not have active targeting, resulting in that the relaxation time, the signal intensity and the duration of the contrast of the contrast agent in the lymphatic system are not satisfactory. Mannose binding protein (MBP) belongs to a lectin receptor protein. This receptor, highly presented in mammalian lung phagocytes, hepatic parenchymal cells and non-parenchymal cells, serum and lymphoid tissues, may bind glycoproteins of which the end is capped with mannose, may incorporate a mannose group in lymph targeted contrast agents, may facilitate the contrast agent to have the function of actively targeting lymphoid tissue, and hence has broad application prospects.

The ideal lymphatic targeted contrast agent needs to meet three conditions: quick injection site clearance rate, long lymphatic dwelling time and high concentrations of lymph node contrast agent. The specific lymphoid contrast agents with active targeting and passive targeting meet the above characteristics. In 2013, the US FDA approved the clinical use of lymphoseek, a target protein that actively targets the mannose receptor of lymphoid macrophages, the lymphoseek is a lymph targeted radionuclide contrast agent that has a mannose fragment attached to dextran molecule and contains a radioactive isotope labeled technetium Tc, to achieve the drawing and positioning of the lymph nodes and the lymphatic vessels. This contrast agent specifically is bound to the lymphoid tissues, demonstrating the successful use of the strategy of binding the mannose binding protein (MBP) receptor rich in the mannose group and lymphoid macrophages in the contrast agent. However, although this radionuclide contrast agent has been applied clinically, the radionuclide contrast agent still has the disadvantages of low sensitivity and large radiotoxicity compared with that of MRI contrast agent. Although CN101862461.B discloses a gadolinium-containing macromolecule contrast agent with a hyaluronic acid as a carrier, and is extended to have lymphatic vascular endothelial hyaluronan receptor-1 (LYVE-1) via the lymphatic vessel to achieve the function of actively targeting the lymphatic system, this patent discloses only the preparation method of the gadolinium-containing macromolecular contrast agent with the hyaluronic acid as the carrier, and there is no data to support that the contrast agent may actively target the lymphatic system and there is no data to support the specific binding of hyaluronic acid to lymphatic vessel hyaluronan receptor-1 (LYVE-1).

Although the lymphoid targeted MRI contrast agent has important clinical needs, in nearly ten years of research, dextran, polyamide polymer, polyethylene glycol polymer or peptide was used as the carrier for the preparation of the lymphatic system contrast agent, which did not enter the approval stage of a new drug, the main reason is that the carrier used above may only target into the lymphatic system depending on the particle size of the material but does not have the binding function with the lymphocyte receptor and may not obtain the contrast agent with the active targeting, quick entry, strong specification and long retention time from the perspective of the lymphoid specific receptor.

SUMMARY OF THE PRESENT INVENTION

The present invention aims to provide a lymphatic targeted contrast agent with a fucoidan as a carrier, a preparation method thereof and an application thereof in view of the problems of no active targeting, slow entry, weak transfer and prolonged residence time in the prior art.

Lymphocyte surface receptors may be bound to a variety of acid polysaccharides, marine polysaccharides and oligosaccharides are rare immune active molecules, polymannuronic acid and polygulonic acid from the marine polysaccharides have strong immunity and activity, moreover, alginate polysaccharides may enhance the phagocytic capacity of lymphatic macrophages (acid phosphatase ACP) via immunological activity. These fucoidans may enhance the binding capacity of the mannose receptor and the phagocytosis capacity of the macrophage, providing the possibility for the present invention to study the NMR contrast agents that actively target the lymphatic system.

The present invention has the following technical solution:

A lymph targeted magnetic resonance contrast agent with a fucoidan as a carrier, wherein
the contrast agent has the following structure: the contrast agent macromolecule takes the fucoidan as the carrier, and a 6-position carboxyl thereof is combined with a mannose receptor MBP recognition group ligand A and a paramagnetic metal chelate ligand B via alkyl, aryl or heterocyclyl as a connection arm, respectively, the contrast agent macromolecule has the following general formula:

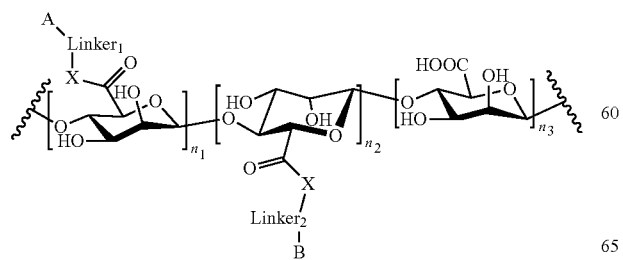

wherein, $n_1$ is an integer, each of $n_2$ and $n_3$ is a positive integer; X is O, N or S; the linker is alkyl, aryl or heterocyclyl; the ligand A is a mannose receptor MBP recognition group; and the ligand B is a paramagnetic metal chelate.

Preferably, the molar content of the ligand A accounts for 0-40% of the original carboxyl of the fucoidan, the molar content of the ligand B accounts for 1-60% of the original carboxyl of the fucoidan, wherein the total of the molar content of the ligand A, the molar content of the ligand B and the molar content of the unreacted carboxyl in the original carboxyl of the fucoidan is 100%.

Preferably, the carrier of the fucoidan is polymannuronic acid PM or polyguluronic acid PG and includes the corresponding carboxylate form thereof, and has a molecular weight of $100\text{-}10^8$ Da.

Preferably, the linker bound to a polysaccharide 6-position carboxyl through an amide bond is an alkyl, aryl or heterocyclic structure having 1 to 20 atoms, and then binds to the mannose receptor MBP recognition group ligand A or the paramagnetic metal chelate ligand B.

Preferably, the uronic acid cyclic carboxylic of the fucoidan is further connected with the mannose receptor MBP recognition group ligand A via an amide bond, and is a mannose and the derivatives thereof in a or configuration with the following specific structure:

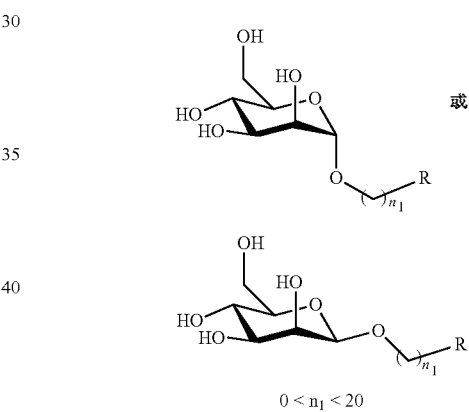

$0 < n_1 < 20$ wherein R may be a variety of functional groups such as hydrocarbyl, carboxyl, amino, hydroxyl, halogen and the like.

Preferably, the paramagnetic metal chelate ligand B is chelated with a metal chelator and paramagnetic metal ions, and the metal chelator is an amino-containing metal chelator with the following structures:

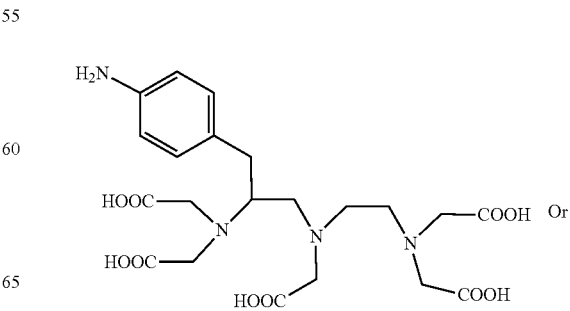

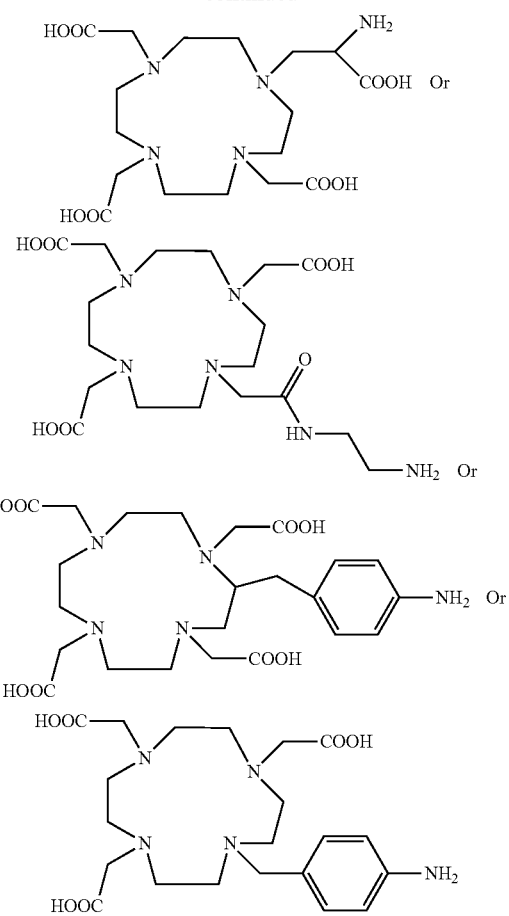

or the metal chelator is an amino-free metal chelator with the following structures:

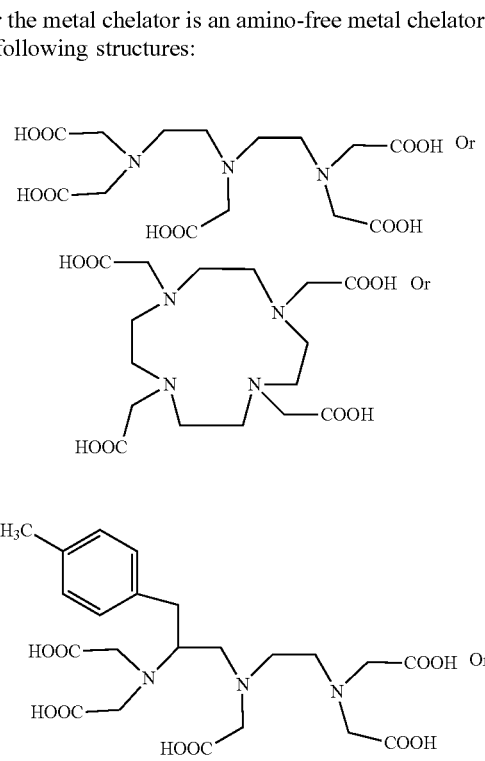

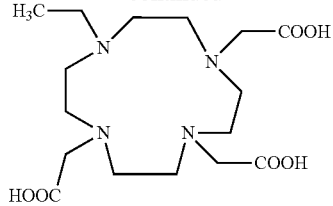

the paramagnetic metal ions used are divalent ions or trivalent ions of Gd, Mn, Cr, Fe, Co, Ni, La, Tc, Dy or Cu.

Another object of the present invention is to disclose a method for preparing a lymph targeted magnetic resonance contrast agent with a fucoidan as a carrier, which comprises the following steps of:

the first step: a fucoidan and an acylation reagent are dissolved in solvent, subsequently, a mannose or the derivatives of the mannose is added, stirred and reacted for 1-24 h, after the reaction is completed, the reaction is quenched, the solution is dialyzed via a dialysis bag to remove small molecular impurities, and an intermediate is obtained via a freeze-drying method, the feeding molar ratio of the mannose or the derivatives of the mannose, the acylation reagent, and all carboxyls of the fucoidan is 0-0.999:0.001-100:1;

the second step: the intermediate and the acylation reagent obtained in the previous step are dissolved in deionized water, added with the amino-containing metal chelator, and stirred and reacted for 1-24 h, after the reaction is completed, the reaction is quenched, an aqueous solution of metal ions is added, a final product is obtained via dialysis and a freeze-drying method, the feeding molar ratio of the metal chelator, the acylation reagent, the metal ions and all carboxyls of the fucoidan is 0.001-100:0.001-100:0.001-100:1.

Preferably, the solvent for the two-step acylation reaction is water, DMSO, or DMF polar aprotic solvent, and the reaction temperature thereof is between 0 and 150° C.

Preferably, the acylation reagent used in the acylation reaction is selected from the group consisting of DMT-MM (4-(4,6-dimethoxytriazin-2-yl)-4-methylmorpholine hydrochloride), EDC (1-(3-Dimethylaminopropyl)-3-ethylcarbodiimide hydrochloride) and CDMT (2-chloro-4,6-dimethoxy-1,3,5-triazine), wherein the structure of DMT-MM is shown in formula (I), the structure of EDC is shown in formula (II), the structure of CDMT is shown in formula (III):

formula (I)

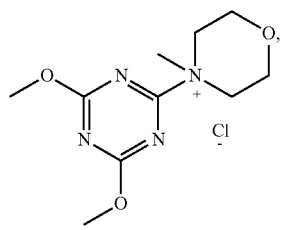

DMT-MM formula (II)

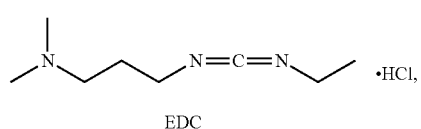

EDC

-continued

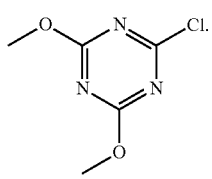

formula (III)

CDMT

-continued

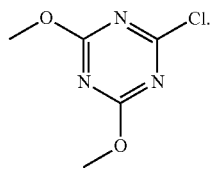

formula (III)

CDMT

The third object of the present invention is to disclose another method for preparing a lymph targeted magnetic resonance contrast agent with a fucoidan as a carrier, which comprises the following steps:

the first step: a fucoidan and an acylation reagent are dissolved in a solvent, then an alkyl diamine compound, a mannose or the derivatives of the mannose are added, stirred and reacted for 1-24 h, after the reaction is completed, the reaction is quenched, the solution is dialyzed and processed with a freeze-drying method to obtain an intermediate, wherein the feeding molar ratio of the mannose or the derivatives of the mannose, the alkyl diamine compound, the acylation reagent and all carboxyls of the fucoidan is 0.001-0.999:0.001-100:0.001-100:1;

the second step: the intermediate and an acylation reagent are dissolved again in the solvent, a metal chelator is added, stirred and reacted for 1-24 h; after the reaction is completed, the reaction is quenched, an aqueous solution of metal ions is added, a final product is obtained after dialysis and lyophilization, the feeding molar ratio of the metal chelator, the acylation reagent, the metal ions and all carboxyls of the fucoidan is 0.001-100:0.001-100:0.001-100:1.

Preferably, the solvent for the two-step acylation reaction is water, DMSO, or DMF polar aprotic solvent, and the reaction temperature thereof is between 0 and 150° C.

Preferably, the acylation reagent used in the acylation reaction is selected from the group consisting of DMT-MM (4-(4,6-dimethoxytriazin-2-yl)-4-methylmorpholine hydrochloride), EDC (1-(3-Dimethylaminopropyl)-3-ethylcarbodiimide hydrochloride) and CDMT (2-chloro-4,6-dimethoxy-1,3,5-triazine), wherein the structure of DMT-MM is shown in formula (I), the structure of EDC is shown in formula (II), the structure of CDMT is shown in formula (III):

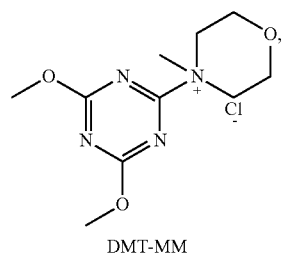

formula (I)

DMT-MM

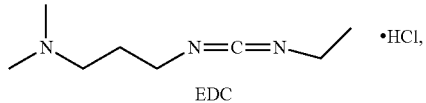

formula (II)

EDC

The fourth object of the present invention is to disclose a use of the contrast agent as described above in the preparation of an agent for diagnosing lymphatic system diseases.

The invention aims to covalently connect a paramagnetic metal chelate with a macromolecule fucoidan to synthesize a lymphatic-specific contrast agent with the function of magnetic resonance detection. The intermediate of the macromolecular contrast agent synthesized by the preparation method of the invention is characterized by using nuclear magnetic resonance; the degree of substitution of each group in the compound is calculated by using the C, N ratios of an elemental analysis method and a peak area integral of a $^1$H NMR spectrum; gadolinium content thereof is determined by ICP-MS; the molecular weight thereof is determined by high performance gel permeation chromatography. After structural characterization, the prepared solution is subcutaneously injected into the first, second and thirdwebbed toes of the hind limbs of a rat and a New Zealand rabbit respectively, nuclear magnetic resonance (MR) scanning is performed every 15-60 min to obtain a MR image.

The invention has the following beneficial effects:

1. A good water-soluble macromolecular contrast agent is prepared by the fucoidan as the carrier, the mannose or the derivatives of the mannose as the mannose receptor (MBP) recognition group, and the paramagnetic metal ion chelate as a nuclear magnetic resonance imaging group, which increases the binding force of lymphoid tissues, the introduction of the mannose or the derivatives of the mannose into the synthesized contrast agent molecule achieves the purpose of the binding to the mannose receptor rich in lymphoid tissue.

2. A lymphangiography experiment is performed with the contrast agent molecules synthetized by the present invention on the models of the rat and New Zealand rabbit, the results show that after the subcutaneous injection of the macromolecular NMR contrast agent, the lymphatic vessels and the lymph nodes are both clearly developed under a MRI scanning, compared with HA-DTPA-Gd with the reference substance hyaluronic acid as the carrier, the signal enhancement rate and the enhancement time of the lymph node, at the side of an animal body, which is injected with this contrast agent, are significantly enhanced, and the clear drawing and precise localization of the lymph nodes and the lymphatic vessels are achieved, which has a great significance in the examination and diagnosis of the lymphatic system disease.

BRIEF DESCRIPTION OF THE DRAWINGS

A: an MR flat scanning image of a lower limb before the injection of the contrast agent; B: an MR image of the lower limb after the injection of the contrast agent for 10 min; C: the MR image of the lower limbs after the injection of the contrast agent for 60 mins; R: right side; L: left side

Figure 10:
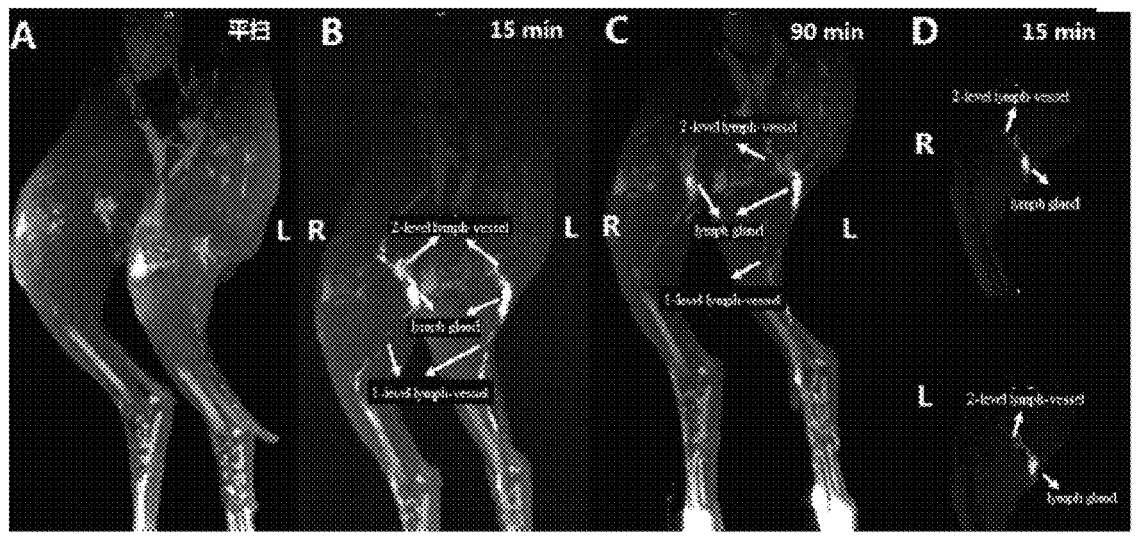
Figure 11:
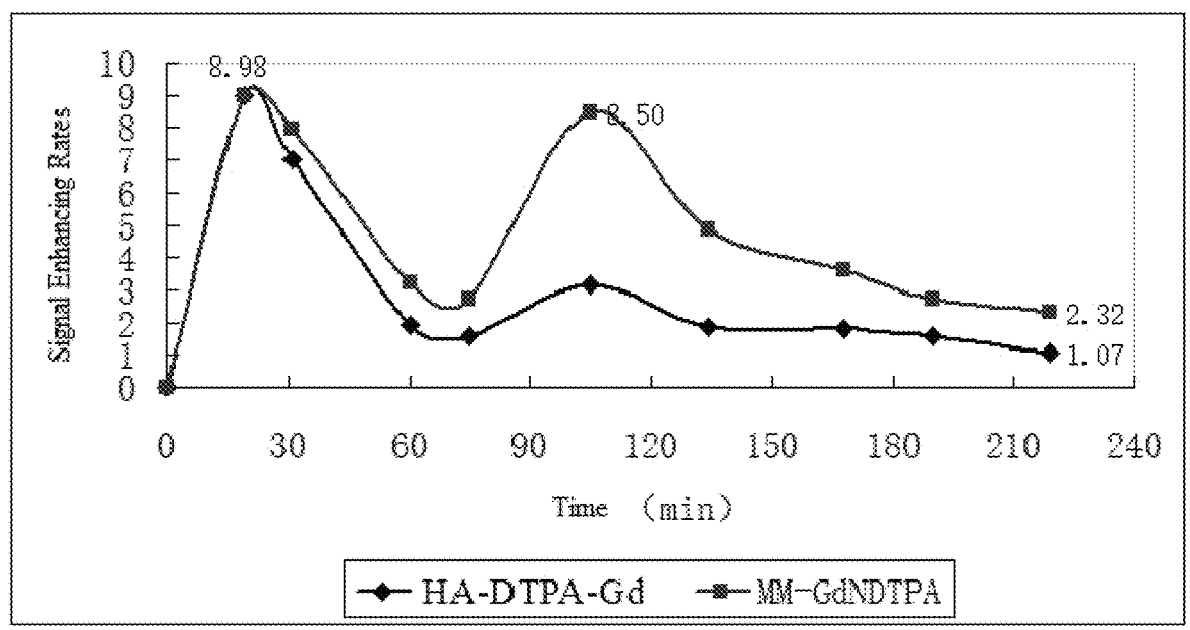
Figure 12:
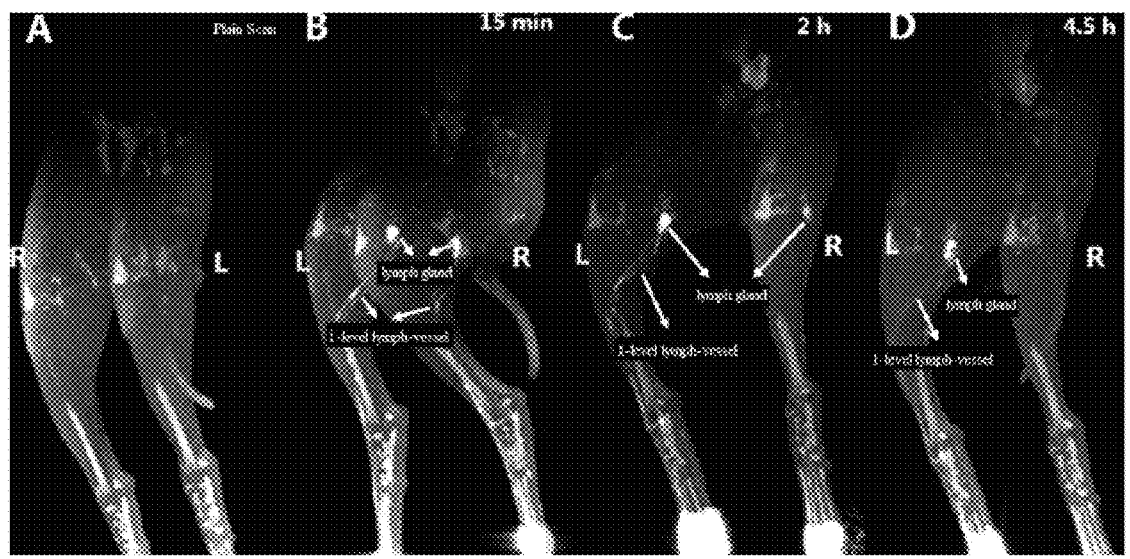
Figure 13:
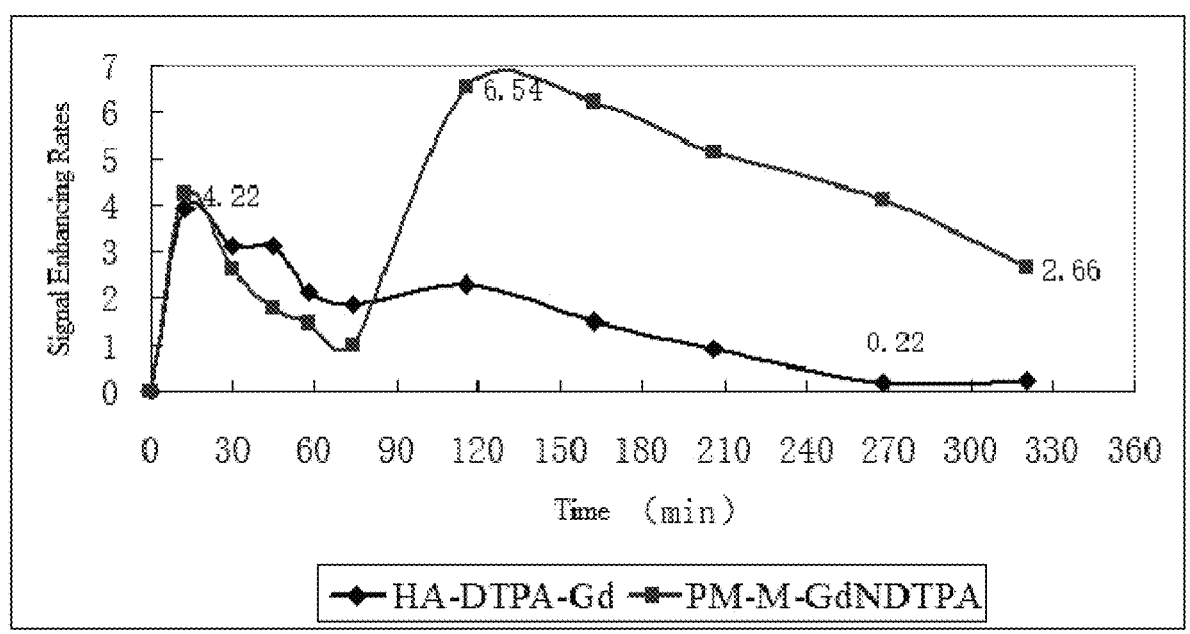
Figure 14:
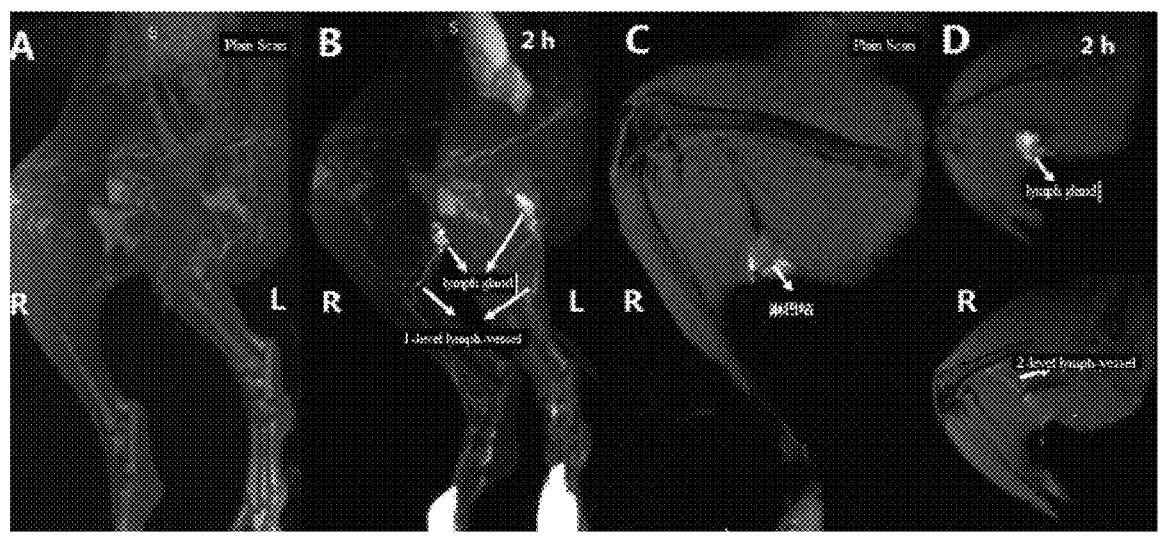
Figure 15:
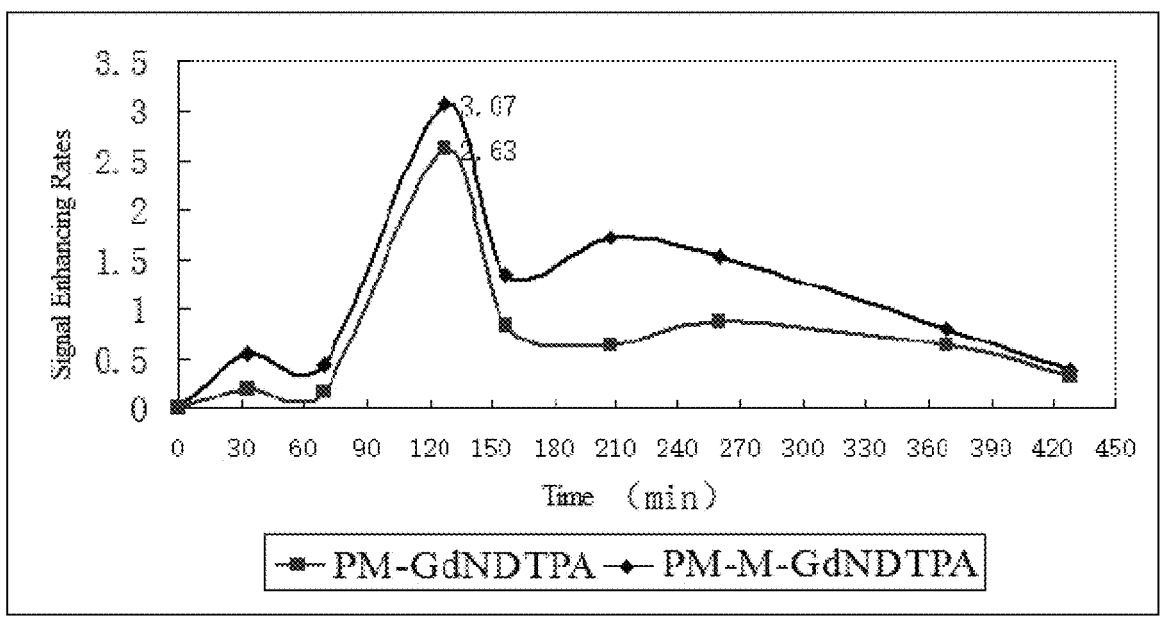
Figure 16:
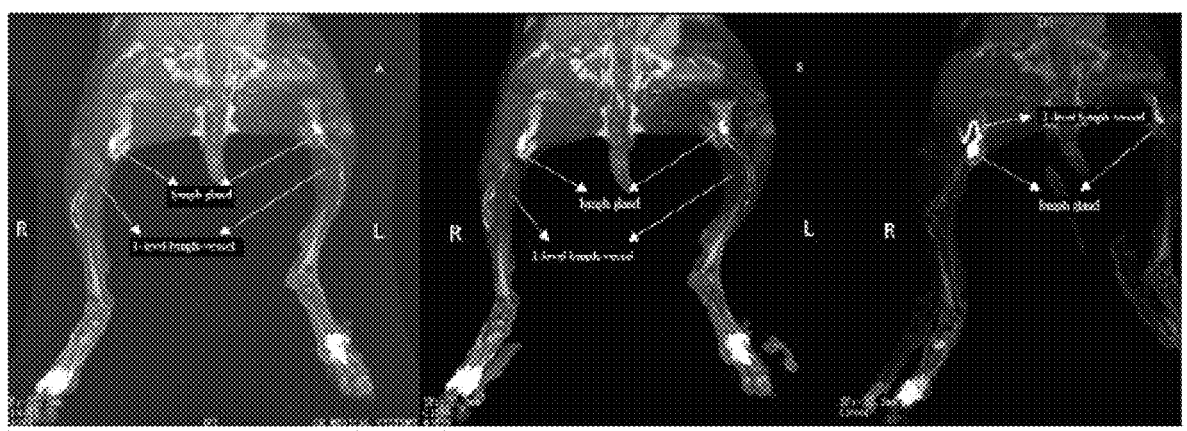

(A) an MR flat scanning image of a lower limb after the injection of contrast agent HA-DTPA-Gd for 15 min; (B) an MR image of the lower limb after the injection of the contrast agent PG-GdDTPA for 15 min;

FIG. 10 is a comparative experimental result diagram of lymph MR imaging of a New Zealand rabbit after the injection of PM-GdNDTPA and HA-DTPA-Gd in Example 3 of the present invention;

A: an MR flat scanning image of a lower limb before injection of a contrast agent; Bran MR image of the lower limb after the injection of the contrast agent for 15 min; C: the MR image of the lower limb after the injection of the contrast agent for 90 min; D: a sagittal MR image of the lower limb after the injection of the contrast agent for 15 min. R: right side; L: left side FIG. 11 is a graph of signal enhancement versus time of PM-GdNDTPA and HA-DTPA-Gd in Example 3 of the present invention;

FIG. 12 is a comparative experimental result diagram of lymph MR imaging of a New Zealand rabbit after the injection of PM-M-GdNDTPA and HA-DTPA-Gd in Example 4 of the present invention;

In the Figure, A: an MR flat scanning image of a lower limb before the injection of a contrast agent; B: an MR image of the lower limb after the injection of the contrast agent for 15 min. C: the MR image of the lower limb after the injection of the contrast agent for 120 min. D: the MR image of the lower limb after the injection of the contrast agent for 4.5 h; R: right side; L: left side FIG. 13 is a graph of signal enhancement versus time of PM-M-GdNDTPA and HA-DTPA-Gd in Example 4 of the present invention;

FIG. 14 is a comparative experimental result of lymph MR imaging of a New Zealand rabbit after the injection of PM-M-GdNDTPA and PM-GdNDTPA in Example 4 of the present invention;

A: an MR flat scanning image of a lower limb before the injection of a contrast agent; B: an MR image of the lower limb after the injection of the contrast agent for 120 min. C: a sagittal MR image of the lower limb before the injection of the contrast agent. D: the sagittal MR image of the lower limb after the injection of the contrast agent for 120 min; R: right side; L: left side FIG. 15 is a graph of signal enhancement versus time of PM-M-GdNDTPA and PM-GdNDTPA in Example 4 of the present invention;

FIG. 16 is a comparative experimental result of lymph MR imaging of a New Zealand rabbit after the injection of PM-M-GdNDTPA and HA-DTPA-Gd in Example 5 of the present invention;

A: an MR image of a lower limb after the injection of the contrast agent for 5 min; B: the MR image of the lower limb after the injection of the contrast agent for 15 min. C: a sagittal MR image of the lower limb after the injection of the contrast agent for 50 min; R: right side; L: left side.

EMBODIMENTS OF THE PRESENT INVENTION

The embodiments of the present invention are as follows:
The technical solution of the present invention is further described below with reference, to the accompanying drawings and embodiments.

When the fucoidan is polymannuronic acid, the specific formula thereof is as follows:

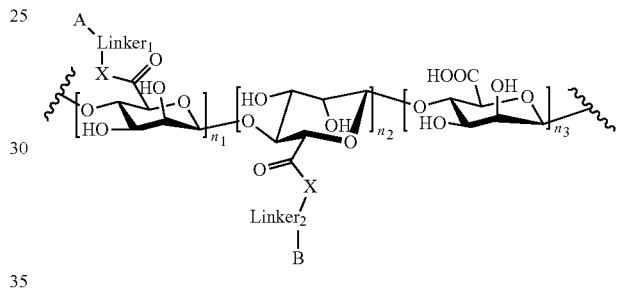

$n_1$ is an integer, $n_2$ and $n_3$ are positive integers, X is O, N or S; a linker is alkyl, aryl or heterocyclyl. A ligand A is a mannose or the derivatives of the mannose. A ligand B is a paramagnetic metal chelate fragment.

When the fucoidan is polyguluronic acid, the specific formula thereof is as follows:

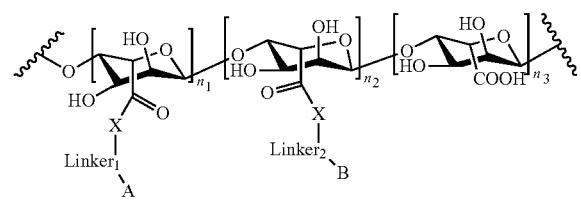

$n_1$ is an integer, $n_2$ and $n_3$ are positive integers, X is O, N or S; the linker is alkyl, aryl or heterocyclyl. The ligand A is the mannose or the derivatives of the mannose. The ligand B is the paramagnetic metal chelate fragment.

Example 1

A carrier of a fucoidan is polymannuronic acid (PM); $n_1=6$, $n_2=16$, $n_3=78$; X is a nitrogen atom (N); a linker$_1$ and a linker$_2$ are dimethyleneamino; the molar content of a mannose receptor (MBP) recognition group (a ligand A) is 0; a ligand B is a metal chelator DTPA and has the molar content of 16%; a paramagnetic metal is gadolinium (Gd); the contrast agent of PM-GdDTPA is obtained. The following reaction processes and steps are included:

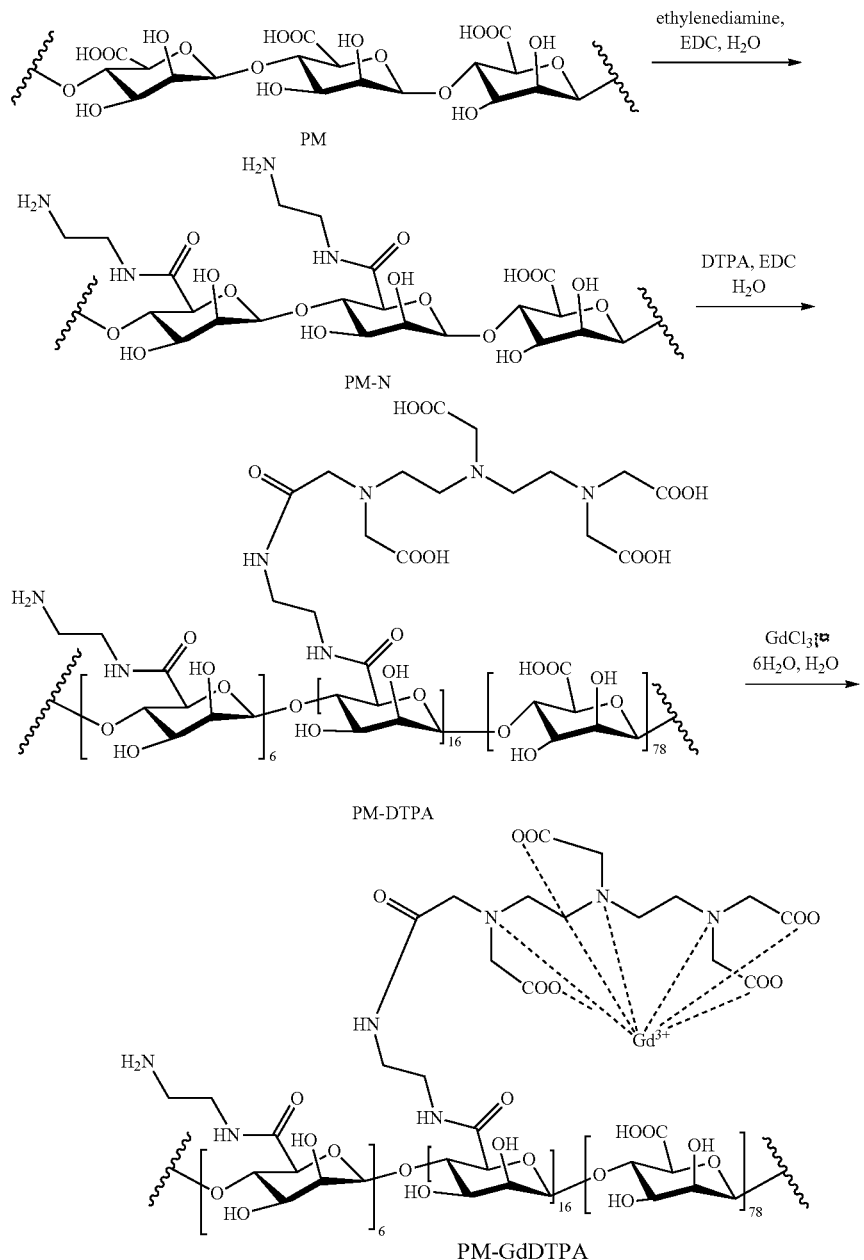

A marine fucoidan poly mannuronic acid (PM) of 1.78 g and an acylation reagent EDC (1.92 g, 10 mmol) are dissolved in deionized water of 50 mL, stirred slowly at room temperature, added with alkyldiamine compounds ethylenediamine (3.0 g, 50 mmol) in batches slowly and reacted at room temperature for 12 h. After the reaction is completed, the solution is placed in a dialysis bag with a cut-off volume of 3,500, and dialyzed in the deionized water for 48 h. After dialysis, the solution is concentrated and lyophilized to obtain a white solid compound PM-N of 1.81 g. The molar ratio of the alkyldiamine compound, the acylation reagent and all carboxyls of the fucoidan is 5:1:1.

The PM-N of 1.81 g and EDC (1.92 g, 10 mmol) are dissolved in the deionized water of 100 mL, added with the metal chelator of diethylenetriaminepentaacetic acid (DTPA) (3.93 g, 10 mmol) under stirring, and reacted at room temperature for 12 h. After the reaction is completed, the solution is placed in the dialysis bag with the cut-off volume of 3,500 and dialyzed in the deionized water for 48 h. After dialysis, the solution is concentrated and lyophilized to obtain a white solid compound PM-DTPA of 2.2 g. The PM-DTPA of 2.2 g is dissolved in the deionized water of 100 mL, and added with $GdCl_3$ of 2.63 g in batches under stirring. After stirred at room temperature for 1 h, the solution is placed in the dialysis bag with the cut-off volume of 3500 and dialyzed in the deionized water for 48 h. After dialysis, the solution is concentrated by rotary evaporation and lyophilized to obtain a white solid compound PM-GdDTPA of 2.3 g. The feeding molar ratio of metal chelator, the acylation reagent, the metal ions and all carboxyls of the fucoidan is 1:1:3:1.

The degree of substitution, the gadolinium content and the molecular weight information of each group of the prepared white solid compound PM-GdDTPA are shown in Table 1:

TABLE 1

Degree of substitution, gadolinium content and molecular weight of each group of PM-GdDTPA of Example 1

| Compounds | Degree of substitution ($mol_{group}/mol_{mannuronic\ acid}$) | | Gadolinium content (W %) | Molecular weight (kDa) |
|---|---|---|---|---|
| | amino | DTPA | | |
| PM | — | — | — | 8.75 |
| PM-N | 0.216 | — | — | 8.32 |
| PM-DTPA | 0.057 | 0.159 | — | 10.03 |
| PM-GdDTPA | 0.057 | 0.159 | 9.71 | 11.0 |

Figure 1:
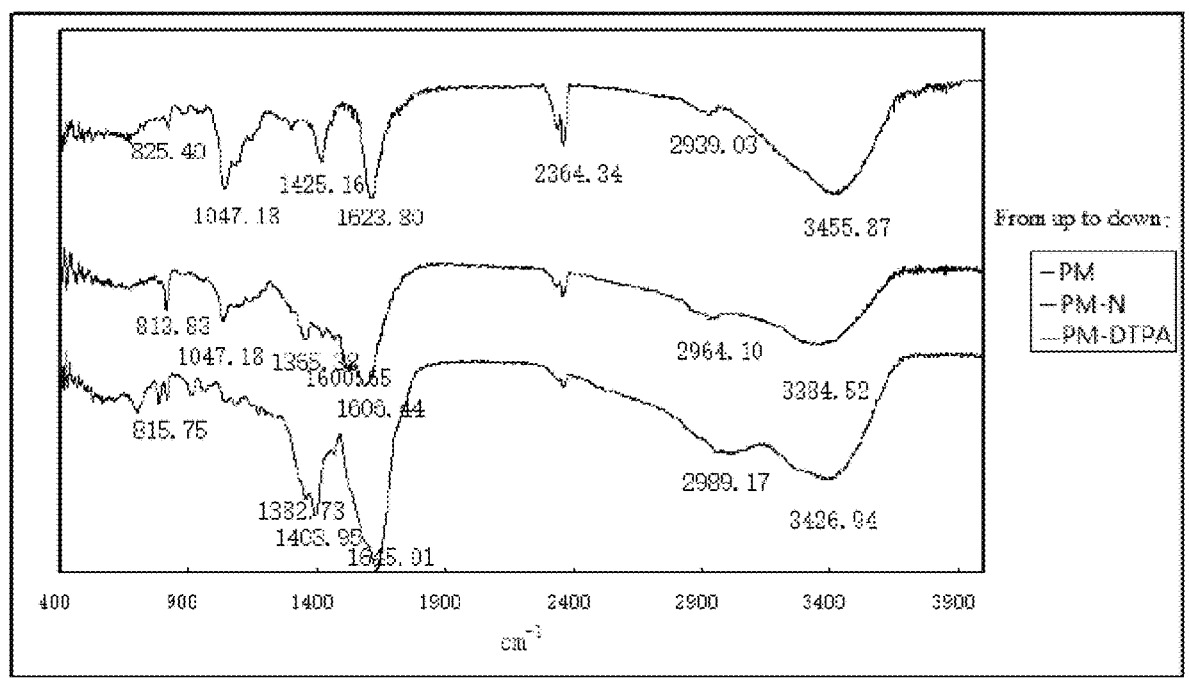
FIG. 1 is an infrared spectrum of a compound synthesized in Example 1 of the present invention.

A infrared spectrum thereof is shown in FIG. 1, as may be seen from FIG. 1: both PM-N and PM-DTPA have similar polysaccharide absorption peaks as PM, namely 3455 cm$^{-1}$, 3884 cm$^{-1}$ and 3426 cm$^{-1}$ are the stretching vibration of hydroxyl 0-H of three compounds; 2939 cm$^{-1}$, 2964 cm$^{-1}$ and 2989 cm$^{-1}$ are the stretching vibration of C—H; 1623 cm$^{-1}$, 1606 cm$^{-1}$ and 1645 cm$^{-1}$ are the asymmetric stretching vibration peaks of carboxyl-COOH; the left and the right of 1400 cm$^{-1}$ are the symmetrical stretching vibration peaks of carboxyl-COOH; 1047 cm$^{-1}$ is the stretching vibration of C—O; 825 cm$^{-1}$, 813 cm$^{-1}$ and 815 cm$^{-1}$ are the characteristic absorption peaks of mannuronic acid. 2364 cm$^{-1}$ is the peak of $CO_2$. 1600 cm$^{-1}$ peak and 1365 cm$^{-1}$ peaks of the intermediate PM-N infrared spectrum are respectively the symmetrical bending vibration peak of the primary amine —$NH_2$ and the stretching vibration peak of the amide bond CN bond, indicating that carboxyamide is connected with an ethylenediamine bond of PM. The decrease of the 1600 cm$^{-1}$ peak and the significant increase of 1645 cm$^{-1}$ in the PM-DTPA infrared spectrum indicate that DTPA is connected to the amino group of PM-N.

Figure 2:
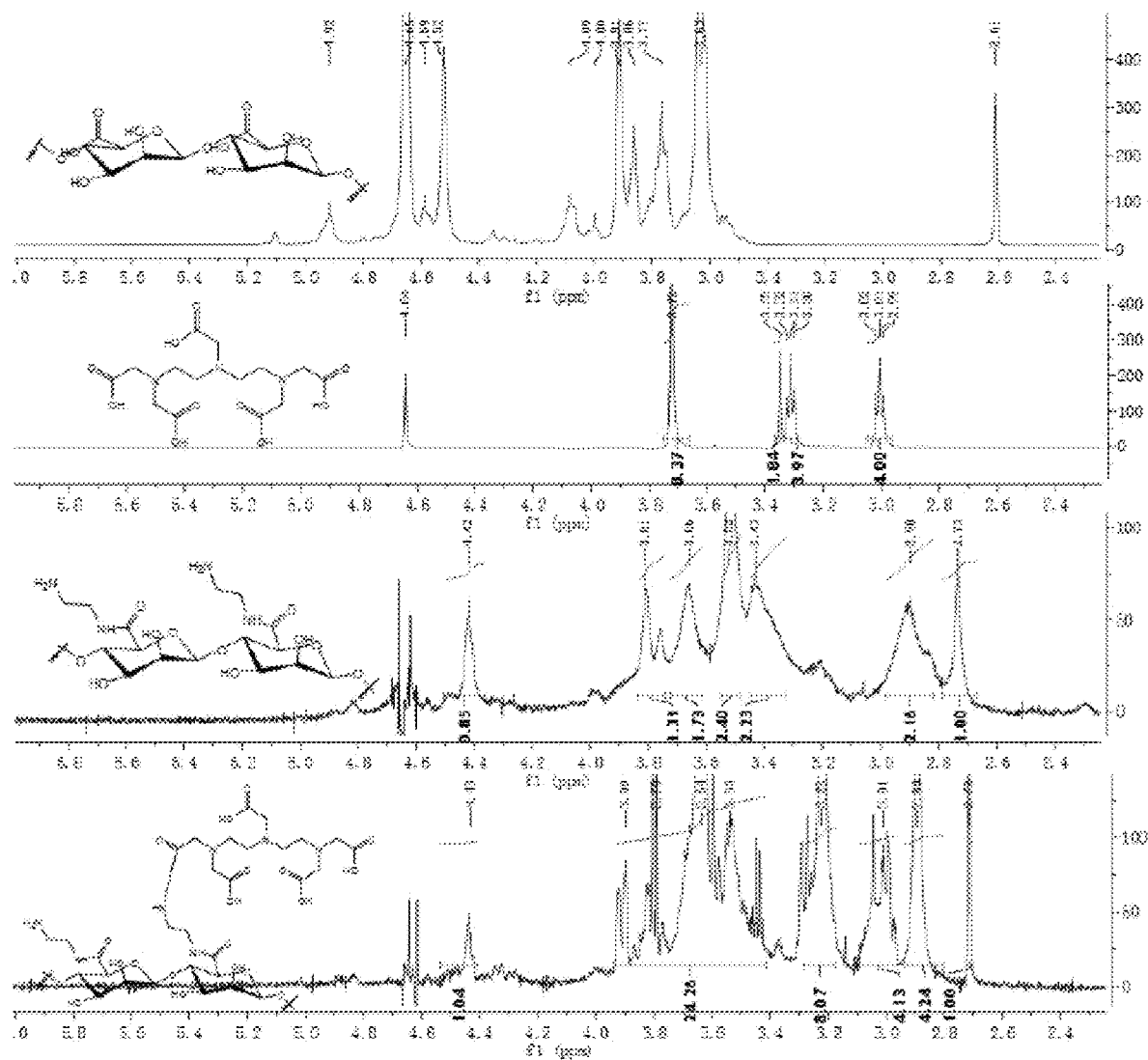
FIG. 2 is a $^1$H NMR spectrum of a compound synthesized in Example 1 of the present invention.
Figure 3:
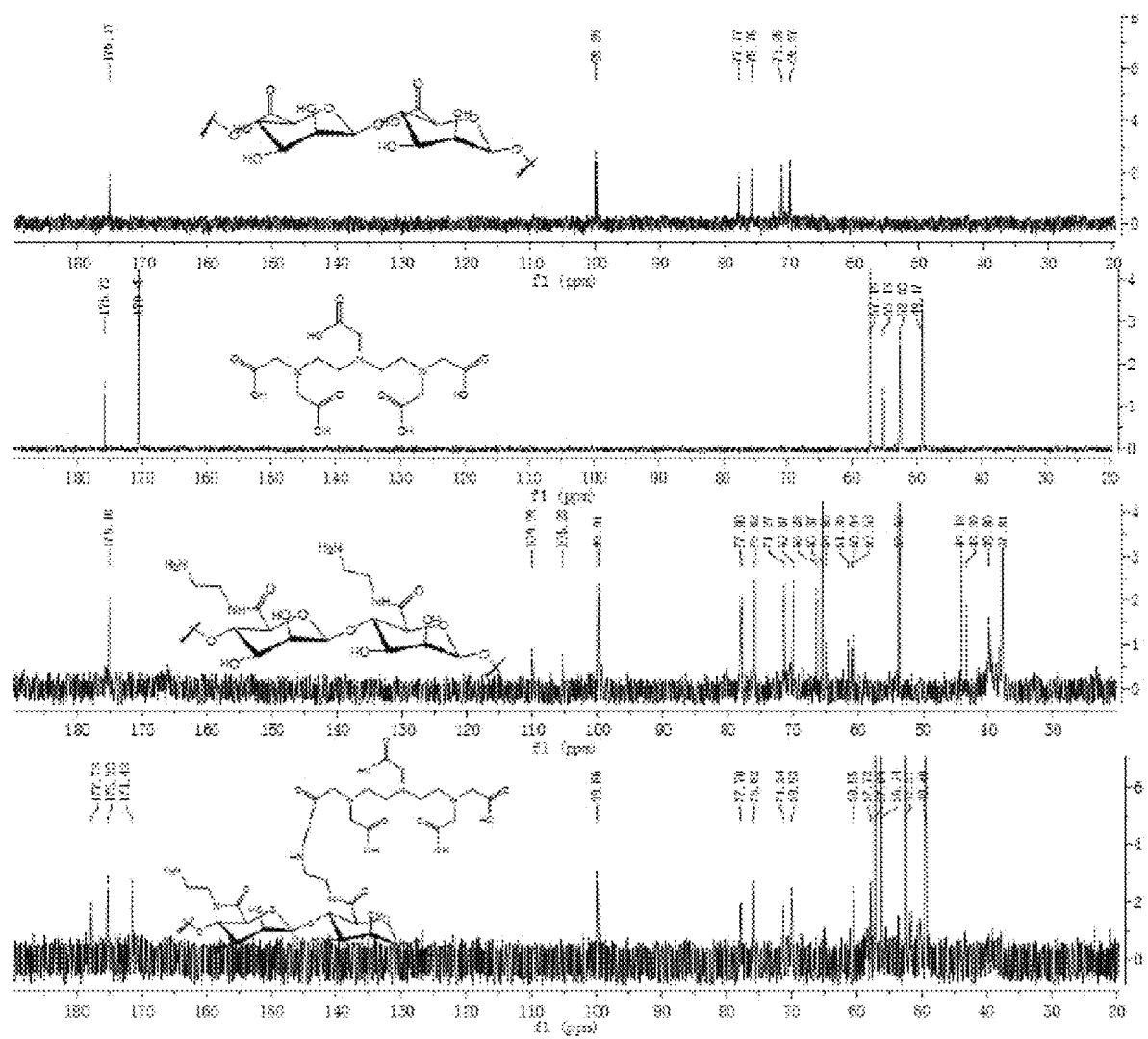
FIG. 3 is a $^{13}$C NMR spectrum of a compound synthesized in Example 1 of the present invention.

The $^1$H NMR spectrum and the $^{13}$C NMR spectrum of the compound synthesized in Example 1 are shown in FIG. 2 and FIG. 3, respectively:

The characteristic peak of polymannuronic acid is the proton peak of sugar ring, the 1-position, 2-position, 3-position, 4-position and 5-position chemical shift values are δ 4.52, 4.09, 3.63, 3.88, 3.77 ppm, respectively. As compared with the PM, the $^1$H NMR spectrum of the intermediate PM-N shows two groups of new peaks of δ 2.90 ppm and δ 2.73 ppm, which are the characteristic peaks of —CO—$CH_2$— and —$CH_2$—$NH_2$ methylene hydrogen, respectively. As compared with PM-N, the $^1$H NMR spectrum of the intermediate PM-DTPA shows the characteristic peaks of DTPA of δ 3.22 ppm and δ 3.01 ppm, which are the characteristic peaks of —CO—$CH_2$— and —$CH_2$—$CH_2$—, respectively.

As compared to PM, the $^{13}$C NMR spectrum of the intermediate PM-N shows two groups of new peaks of δ 44.18-43.39 ppm and δ 39.80-37.81 ppm, which are the characteristic peaks of —CO—$CH_2$— and —$CH_2$—$NH_2$ methylene carbon, respectively. Compared with the PM-N, the $^{13}$C NMR spectrum of an intermediate PM-DTPA shows the carbonyl carbon characteristic peaks of δ 177.73 and 171.43 ppm and the methylene carbon characteristic peaks of 57.09, 56.14, 52.51 and 49.40 ppm of DTPA.

Figure 8:
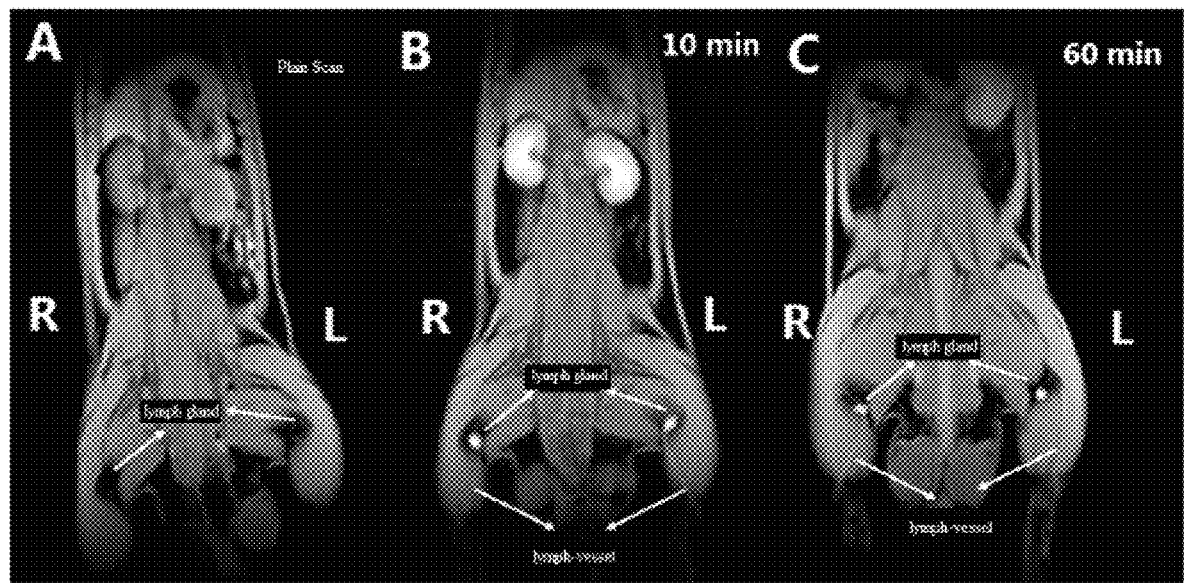
FIG. 8 is a MR developing diagram of lymph nodes and lymphatic vessels of lower limbs at both sides of a healthy rat after the subcutaneous injection of macromolecular contrast agent PM-GdDTPA in Example 1 of the present invention.

A healthy rat weighing 205 g is provided. The rat is intramuscularly anesthetized with ketamine (80 mg/kg) and diazepam (5 mg/kg) and fixed on an operating table for MRI flat scanning. Corresponding parameters are: 3D Fast TOF-SPGRCE-MRA sequence scan, Flip Angle 30°, TE 1.6 ms, TR 4.5 ms, field of view 280×280 mm, matrix 360×224, layer thickness 1.0 mm, slah70, and NEX 2. Then, the macromolecular contrast agent of PM-GdDTPA (30 mg/L) is injected subcutaneously into the first, the second and the third webbed toes of the feet of the rat, each injection is 0.2 ml, 3D enhanced scanning is performed. The related parameters of enhanced scan sequence are consistent with those of the flat scanning, scanning is performed every 15 minutes, a total of the scanning is 5 times. the lymph nodes and the lymphatic MR imaging images of the lower limbs at both sides of the healthy rat in Example 1 after the subcutaneous injection of the macromolecular contrast agent of PM-GdDTPA are shown in FIG. 8, in the figure, A: an MR flat scanning image of a lower limb before the injection of the contrast agent; B: a MR image of the lower limb after the injection of the contrast agent for 10 min. C: the MR image of the lower limb after the injection of the contrast agent for 60 min. R: right side; L: left side.

The result shows that there is no enhancement signal in popliteal lymph nodes before the injection of the contrast agent. However, after the injection of the PM-GdDTPA for 10 min, the signals of level-1 lymphatic vessels and lymph nodes on both sides are rapidly strengthened, the lymph nodes are clearly developed and show a regular oval. After the injection of the contrast agent for 60 min, the lymph nodes at both sides are still developed clearly. This indicates that the PM-GdDTPA may rapidly enhance the MR signal intensity of the lymph nodes and the lymphatic vessels, to achieve a clear development of the lymphatic system; at the same time, this shows a longer lymph node resident capacity, lymph node development time may be up to one hour. This indicates that the PM-GdDTPA has the advantages of rapid lymphatic system development and longer development time.

Example 2

A carrier of a fucoidan is polyguluronic acid (PG); $n_1$=13 $n_2$=19 $n_3$=46; X is a nitrogen atom (N); a linker$_1$ and a linker$_2$ are dimethyleneamino; mannose receptor (MBP) recognition group (a ligand A) has the molar content of 0; a ligand B is a metal chelator DTPA and has the molar content of 19%; a paramagnetic metal is gadolinium (Gd); the contrast agent of PG-GdDTPA is obtained. The following reaction processes and steps are provided:

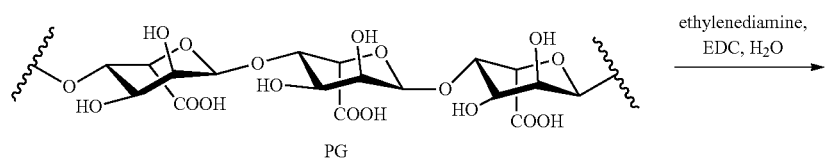

PG

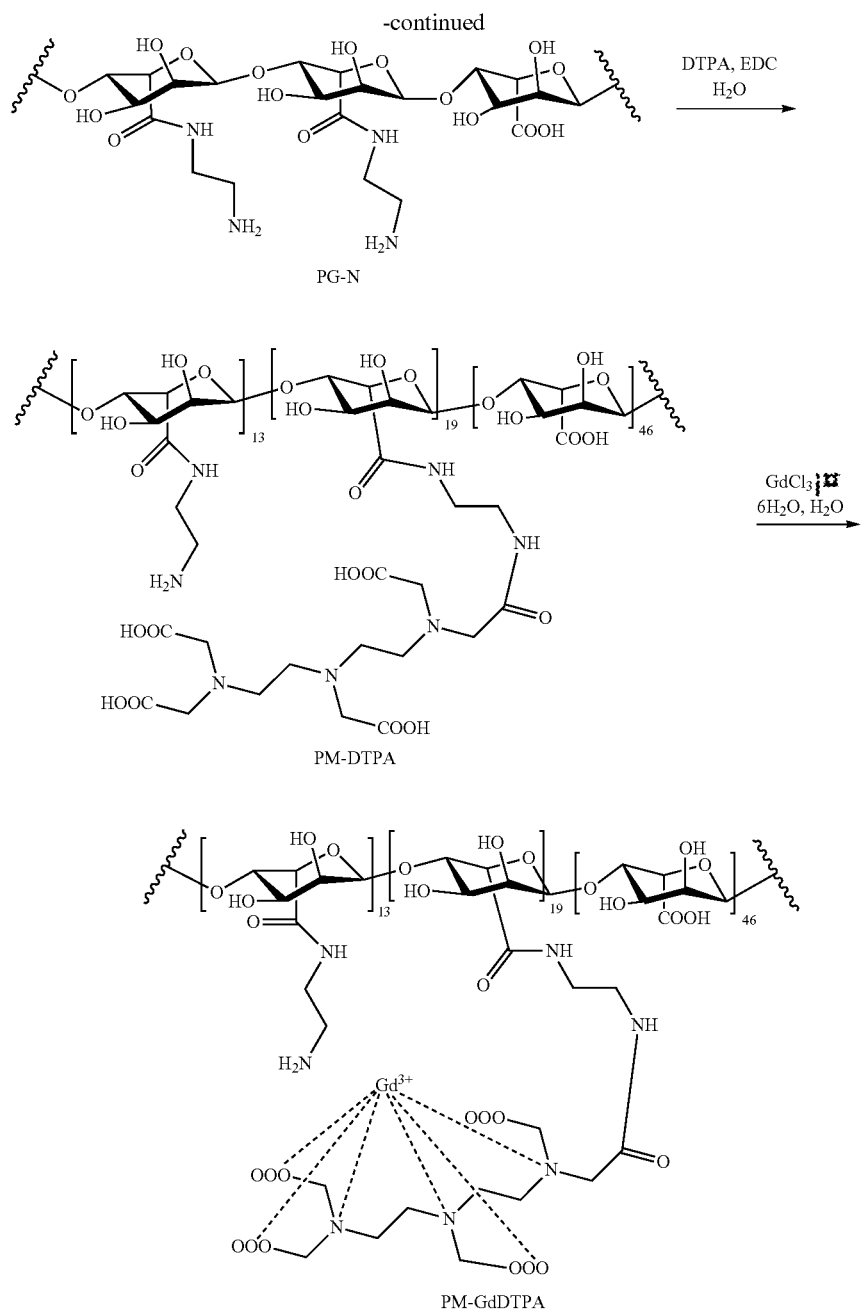

A marine fucoidan polyglucuronic acid (PG) of 2.3 g and an acylation reagent EDC (2.48 g, 12.9 mmol) are dissolved in deionized water of 70 mL, added with alkyldiamine compounds of ethylene glycol Amine (3.8 g, 63.3 mmol) at room temperature under stirring slowly in batches, and reacted at the room temperature for 12 h. After the reaction is completed, a solution is placed in a dialysis bag with a cut-off volume of 3,500 and dialyzed in the deionized water for 48 h. After dialysis, the solution is concentrated and lyophilized to obtain a white solid compound PG-N of 2.01 g. The molar ratio of alkyldiamine compound, the acylation reagent and all carboxyls of the fucoidan is 5:1:1.

The PG-N of 2.01 g and the acylation reagent EDC (2.48 g, 12.9 mmol) are dissolved in the deionized water of 100 mL, added with the metal chelator of diethylenetriamine-pentaacetic acid (DTPA) (4.38 g, 11 mmol) under stirring in batches slowly, and reacted at room temperature for 12 h. After the reaction is completed, the solution is placed in the dialysis bag with the cut-off volume of 3,500 and dialyzed in the deionized water for 48 h. After dialysis, the solution is concentrated and lyophilized to obtain the a white solid compound PG-DTPA of 2.5 g. The prepared PG-DTPA of 2.5 g is dissolved in the deionized water of 100 mL, and added with GdCl3 of 3.0 g under stirring in batches. After stirred at room temperature for 1 h, the solution is placed in the dialysis bag with the cut-off volume of 3500 and dialyzed in the deionized water for 48 h. After dialysis, the solution is concentrated and lyophilized to obtain a white solid compound PG-GdDTPA of 2.8 g.

TABLE 2

Degree of substitution, gadolinium content and molecular weight of each group PG-GdDTPA of Example 2

| Compounds | Degree of substitution ($mol_{group}/mol_{mannuronic\ acid}$) | | Gadolinium content (W %) | Molecular weight (kDa) |
|---|---|---|---|---|
| | Amino | DTPA | | |
| PG | — | — | — | 9.25 |
| PG-N | 0.216 | — | — | 9.78 |
| PG-DTPA | 0.132 | 0.194 | — | 10.13 |
| PG-GdDTPA | 0.132 | 0.194 | 8.47 | 10.83 |

A healthy New Zealand white rabbit weighing 3.16 kg is provided. The New Zealand white rabbit is intramuscularly anesthetized with ketamine (80 mg/kg, 1.6 ml) and diazepam (5 mg/kg, 1 ml). The rabbit is fixed on a rabbit operating table for MRI flat scanning. Corresponding parameters are: 3D Fast TOF-SPGRCE-MRA sequence scanning, Flip Angle 30°, TE 1.6 ms, TR 4.5 ms, field of view 280×280 mm, matrix 360×224, layer thickness 1.0 mm, slah70, NEX 2. PG-GdDTPA synthesized in Example 2 and HA-DTPA-Gd physiological saline solution are then injected subcutaneously into the first, the second and the third webbed toes of the left and right hind limbs of the New Zealand rabbit. Each injection is 0.1 ml, gadolinium concentration is 0.03 mmol/nil. After the injection of the contrast agent, scanning is performed every 15-60 min within 3.5 h, a total of scanning is 9 times.

Figure 9:
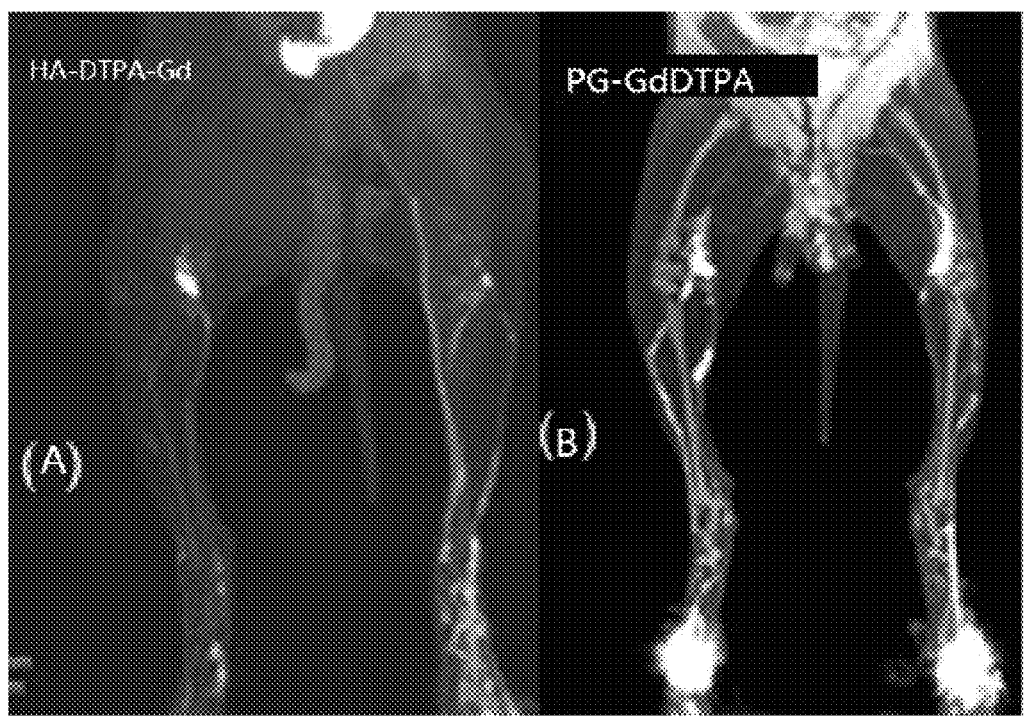
FIG. 9 is a comparative experimental result diagram of an MR imaging of a New Zealand rabbit after the injection of PG-GdDTPA and HA-DTPA-Gd in Example 2 of the present invention.

FIG. 9 is a comparative experimental result diagram of a lymph MR imaging of a New Zealand rabbit after the injection of PG-GdDTPA and HA-DTPA-Gd (macromolecule contrast agent prepared by ZL201010205001.1) in Example 2, in the figure, A: a MR flat scanning image of the lower limb after the injection of the contrast agent of HA-DTPA-Gd for 15 min; B: a MR image of the lower limb after the injection of the contrast agent of PG-GdDTPA for 15 min;

After the injection of the contrast agent of PG-GdDTPA for 15 min, the signals of the lymphatic vessels and the lymph nodes at both sides are rapidly enhanced; three level-1 lymphatic vessels are clearly developed, and intersected at popliteal lymph nodes; a level-2 lymphatic vessel is clearly developed similarly, and extended to an abdominal cavity. However, the signals of the lymphatic vessels and the lymph nodes at both sides are blurred after the injection of the contrast agent of HA-DTPA-Gd1 for 5 min, the level-2 lymphatic vessel is not clearly developed.

Example 3

A carrier of a fucoidan is polymannuronic acid (PM); $n_1=0$ $n_2=29$ $n_3=71$; X is a nitrogen atom (N); a $linker_2$ is benzyl; a mannose receptor (MBP) recognition group (a ligand A) has a molar content of 0; a ligand B is a metal chelator 1-(p-aminobenzyl)-DTPA and has a molar content of 29%; a paramagnetic metal is gadolinium (Gd); the contrast agent of PM-GdNDTPA is obtained. The following reaction processes and steps are provided:

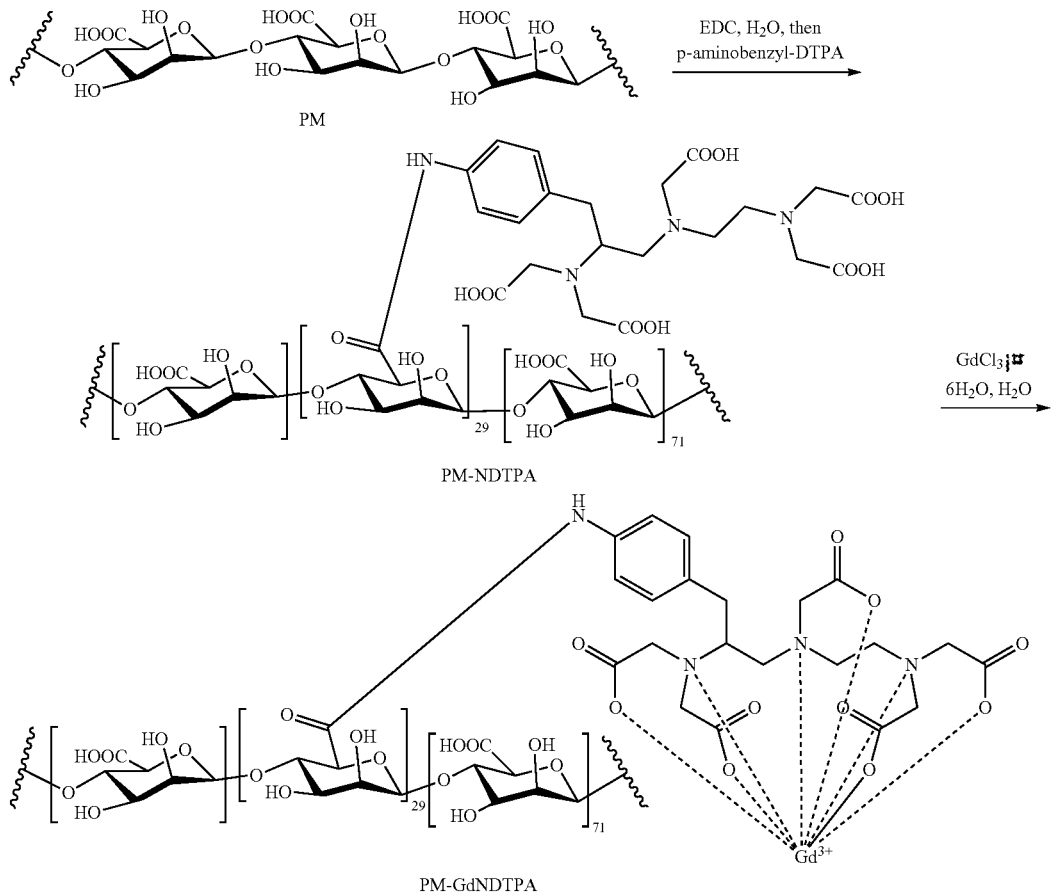

PM-GdNDTPA

? indicates text missing or illegible when filed

A marine fucoidan polymannuronic acid polymannuronic acid PM (2.6 g, 15 mmol) and an acylation reagent EDC (2.88 g, 15 mmol) are dissolved in a deionized water of 100 mL and added with metal chelator 1-(p-aminobenzyl)-DTPA hydrochloride (1.93 g, 3 mmol) under stirring. After stirred at room temperature for 12 h, $K_2CO_3$ (8.3 g, 60 mmol) is added to the solution and continues to be stirred for 0.5 h. After the reaction is completed, a solution is placed in a dialysis bag with a cut-off volume of 3,500 and dialyzed in the deionized water of 5 L, water is changed every 6 h, a total of water changes is 5 times. After dialysis, the solution is concentrated and lyophilized to obtain a white solid compound PM-NDTPA of 2.8 g. the PM-NDTPA of 2.8 g prepared by the reaction is dissolved in the deionized water of 100 mL, and added with GdCl3 6H2O (0.93 g, 2.5 mmol) under stirring in batches, the pH of 5% NaOH solution is adjusted to be 5~6, after stirred at room temperature for 1 h, the solution is placed in the dialysis bag with the cut-off volume of 3500, and dialyzed in the deionized water of 5 L, the water is changed every 6 h, a total of water changes is 5 times. After dialysis, the solution is concentrated and lyophilized to obtain a white solid compound PM-GdNDTPA of 2.7 g. The molar ratio of the metal chelator, the acylation reagent, metal ions and all carboxyls of the fucoidan is 0.2:1:0.17:1;

Table 3 shows the degree of substitution, the gadolinium content, and the molecular weight of each group of the obtained white solid compound PM-GdNDTPA.

TABLE 3

Degree of substitution, gadolinium content and molecular weight of each group of PM-GdNDTPA prepared in Emdodiment 3

| Compounds | Degree of Substitution of 1-(p-Aminobenzyl)-DTPA ($mol_{group}/mol_{mannuronic\ acid}$) | Gadolinium content (W %) | Molecular weight (kDa) |
|---|---|---|---|
| PM | — | — | 8.75 |
| PM-NDTPA | 0.29 | — | 12.72 |
| PM-GdNDTPA | 0.29 | 8.41 | 13.8 |

Figure 4:
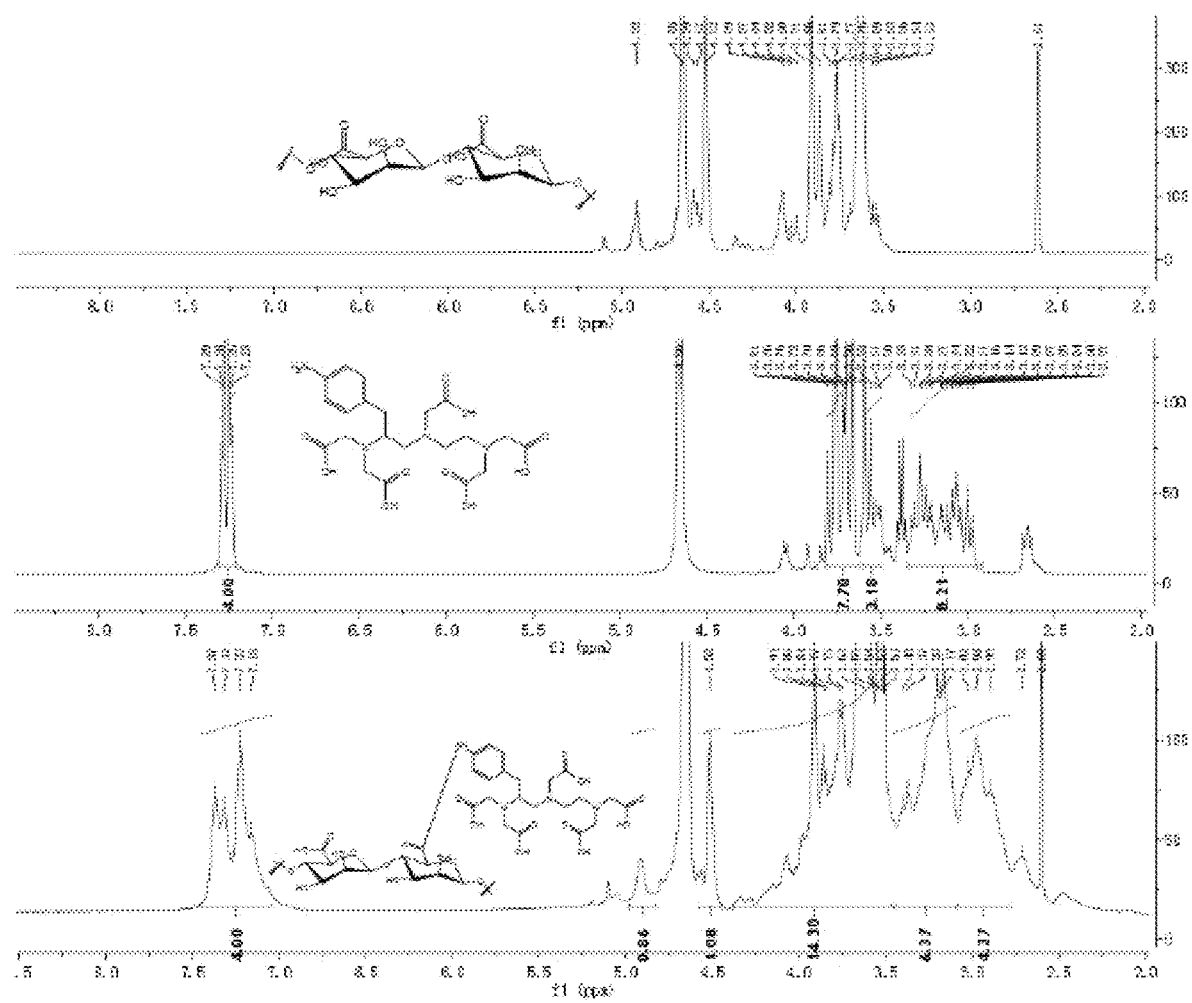
FIG. 4 is a $^1$H NMR spectrum of a compound synthesized in Example 3 of the present invention.
Figure 5:
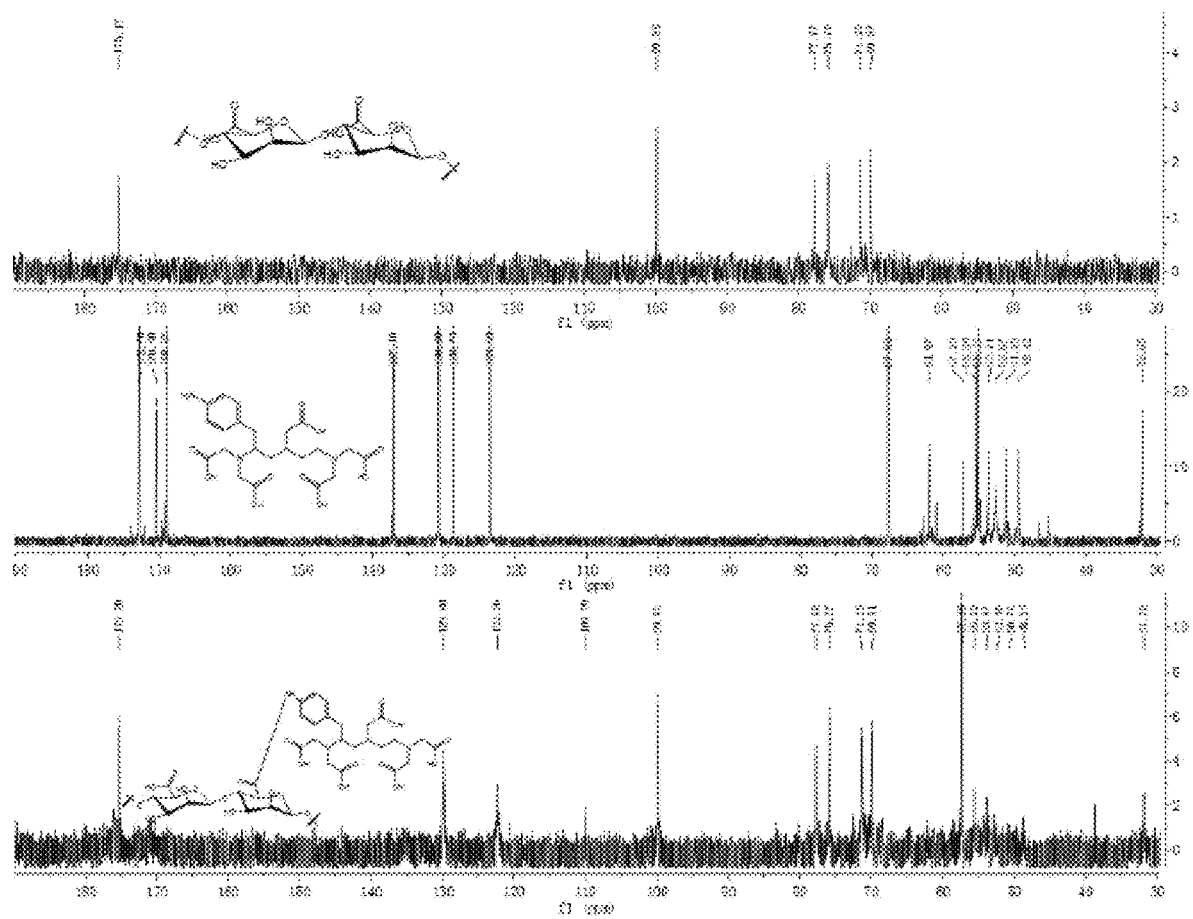
FIG. 5 is a $^{13}$C NMR spectrum of a compound synthesized in Example 3 of the present invention.

The $^1H$ spectrum and the $^{13}C$ NMR spectrum of the compounds synthesized in Example 3 are shown in FIGS. 4 and 5:

Compared to PM, the $^1H$ NMR spectrum of an intermediate PM-NDTPA shows four groups of new peaks: the d peaks at δ 7.34 ppm and δ 7.17 ppm are the two groups of hydrogen signals on the 1-(p-aminobenzyl)-DTPA benzene ring; the two groups of peaks of 3.37-3.17 ppm and 3.02-2.90 ppm are the benzylic position on 1-(p-aminobenzyl)-DTPA and —$CH_2$—$NH_2$ methylene hydrogen signal; —CO—CH2-methylene hydrogen signal coincides with sugar ring hydrogen signal.

In the $^{13}C$ NMR spectrum of an intermediate PM-NDTPA, δ 129.80, 122.26, 109.99, 99.85 ppm are the four carbon signal peaks of the benzene ring on 1-(p-aminobenzyl)-DTPA; δ 31.78 ppm is the methylene carbon signal of the benzylic position on 1-(p-aminobenzyl)-DTPA; δ 57.38-48.54 ppm peaks are the characteristic peaks of —CO—$CH_2$— and —$CH_2$—$NH_2$ methylene carbons on 1-(p-aminobenzyl)-DTPA.

A healthy New Zealand white rabbits weighing 3.12 kg is provided. The New Zealand white rabbit is intramuscularly anesthetized with ketamine (80 mg/kg, 1.6 ml) and diazepam (5 mg/kg, 1 ml). The rabbit is fixed on a rabbit operating table for MRI flat scanning. The corresponding parameters are: 3D Fast TOF-SPGRCE-MRA sequence scanning, Flip Angle 30°, TE 1.6 ms, TR 4.5 ms, field of view 280×280 mm, matrix 360×224, layer thickness 1.0 mm, slah70, and NEX 2. Then, the PM-GdNDTPA and HA-DTPA-Gd physiological saline solutions synthesized in Example 3 are subcutaneously injected into the first, the second and the third webbed toes of the left and right hind limbs of the New Zealand rabbit. Each injection is 0.1 ml, gadolinium concentration is 0.03 mmol/ml. After the injection of the contrast agent for 3.5 h, the scanning is performed every 15-60 min within 3.5 h, a total of the scanning is 9 times.

FIG. 10 is a comparative experimental result diagram of a lymph MR imaging of a New Zealand rabbit of PM-GdNDTPA and HA-DTPA-Gd (a macromolecular contrast agent prepared by ZL201010205001.1), in the figure, A: an MR flat scanning image of a lower limb before the injection of the contrast agent; B: an MR image of the lower limb after the injection of the contrast agent for 15 min; C: the MR image of the lower limb after the injection of the contrast agent for 90 min; D: a sagittal MR image of the lower limb after the injection of the contrast agent for 15 min; R: right side; L: left side.

After the injection of the contrast agent for 15 min, the signals of the lymphatic vessels and the lymph nodes at both sides are rapidly enhanced. Three level-1 lymphatic vessels are clearly developed, and intersected in popliteal lymph nodes; level-2 lymphatic vessels are clearly developed similarly, and extended to an abdominal cavity. After the injection of the contrast agent for 90 min, the signal intensity of right lymph nodes and the lymphatic vessels injected with HA-DTPA-Gd is significantly weakened while left lymph nodes and level-1 and level-2 lymphatic vessels injected with PM-GdNDTPA is still maintained at a clear development.

A signal enhancement versus time curve (FIG. 11) shows that the left lymph nodes injected with PM-GdNDTPA and the right lymph nodes injected with HA-DTPA-Gd both have two MR signal enhancement peaks, which occur at 15 min and 120 min, respectively. The MR signal enhancement peaks of the lymph nodes on both sides at 15 min show significant similarities in a peak shape, a peak value and a peak appearance time, the peak value of the signal enhancement rate is up to about 9. However, the MR signal enhancement peak of the lymph nodes at 120 min shows a significantly higher signal enhancement ratio in the left lymph nodes than in the right lymph nodes, the peak value in the left side is about 3 times as much as that in the right side. The lymph nodes at the left side still have a signal enhancement rate of 2.32 after 3.5 h, indicating that PM-GdNDTPA has excellent lymph node resident capacity.

Example 4

A carrier is polymannuronic acid (PM); $n_1=15$ $n_2=17$ $n_3=68$; X is a nitrogen atom (N); a $linker_1$ is dimethylene and a $linker_2$ is benzyl; a ligand A is mannose (M) and has the molar content of 15%; a ligand B is the metal chelator 1-(p-aminobenzyl)-DTPA and has the molar content of 17%; a paramagnetic metal is gadolinium (Gd); PM-M-GdNDTPA of a contrast agent is obtained. The following reaction processes and steps are included:

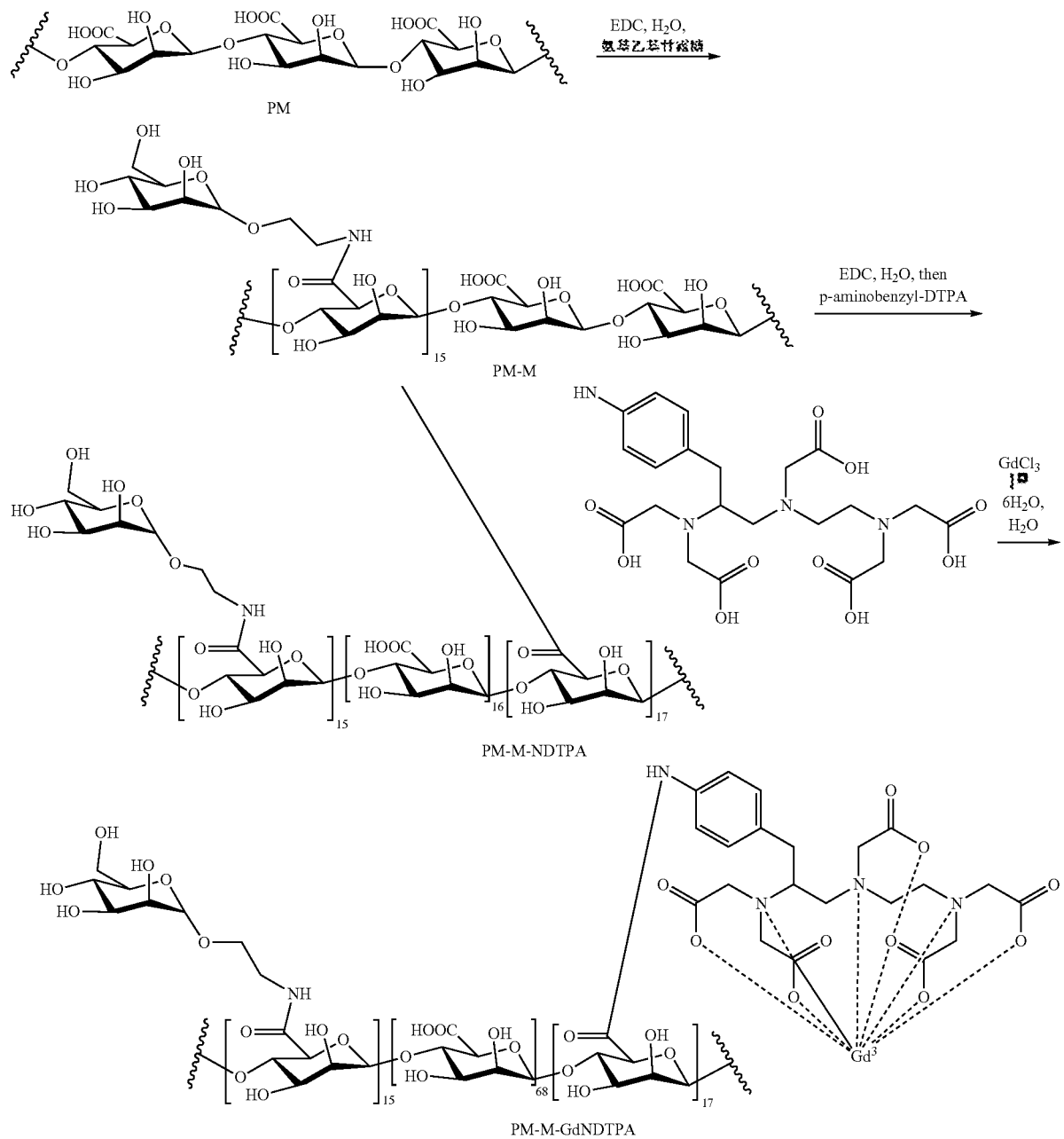

A marine fucoidan polymannuronic acid (PM, 3.52 g, 20 mmol) and an acylation reagent EDC (3.83 g, 20 mmol) are dissolved in deionized water of 50 ml and added with 1-O-Aminoethyl mannose (1.42 g, 5 mmol) under stirring in batches slowly and stirred and reacted at room temperature for 12 h. After the reaction is completed, $K_2CO_3$ (8.3 g, 60 mmol) is added to the solution and stirred for 0.5 h; the solution is placed in a dialysis bag with a cut-off volume of 3,500 and dialyzed in the deionized water of 5 L, water is changed every 6 h, a total of water changes is 5 times. After dialysis, the solution is concentrated and lyophilized to obtain a white solid compound PM-M of 3.4 g. The molar ratio of the derivatives of the mannose, the acylation reagent, all carboxyls of the fucoidan is 0.25:1:1.

An intermediate PM-M of 3.5 g and EDC (1.92 g, 10 mmol) prepared in the previous step are dissolved in the deionized water of 100 mL, added with acid salt (1.93 g, 3 mmol) of 1-(p-aminobenzyl)-DTPA under stirring, and stirred and reacted at room temperature for 12 h. After the reaction is completed, $K_2CO_3$ (8.3 g, 60 mmol) is added to the solution and stirred for 0.5 h. The solution is placed in a dialysis bag with a cut-off volume of 3,500 and dialyzed in the deionized water of 5 L, the water is changed every 6 h, a total of water changes is 5 times. After dialysis, the solution is concentrated and lyophilized to obtain a white solid compound PM-M-NDTPA of 3.1 g. The prepared PM-M-NDTPA of 3 g is dissolved in the deionized water of 100 ml, $GdCl_3 \cdot 6H_2O$ (0.93 g, 2.5 mmol) is added under stirring in batches, the PH of 5% NaOH solution is adjusted to be 5~6. After stirred at room temperature for 1 h, the solution is placed in the dialysis bag with the cut-off volume of 3500 and dialyzed in the deionized water of 5 L, the water is changed every 6 h, a total of water changes is 5 times. After dialysis, the solution is concentrated and lyophilized to obtain a white solid compound PM-M-GdNDTPA of 2.76 g. The molar ratio of a metal chelator, the acylation reagent, metal ions and all carboxyls of the fucoidan is 0.15:0.5: 0.125:1, Table 4 shows the degree of substitution, the gadolinium content and the molecular weight of each group of the prepared white solid compound PM-M-GdNDTPA.

TABLE 4

Degree of substitution, gadolinium content and molecular weight of each group of PM-M-GdNDTPA prepared in Example 4

| Compounds | Degree of Substitution (mol$_{group}$/mol$_{mannuronic\ acid}$) | | Gadolinium content (W %) | Molecular weight (kDa) |
|---|---|---|---|---|
| | Mannose | p-Amino-benzyl-DTPA | | |
| MM | — | — | — | 8.75 |
| PM-M | 0.15 | — | — | 8.99 |
| PM-M-NDTPA | 0.15 | 0.17 | — | 10.03 |
| PM-M-GdNDTPA | 0.15 | 0.17 | 3.81 | 10.41 |

Figure 6:
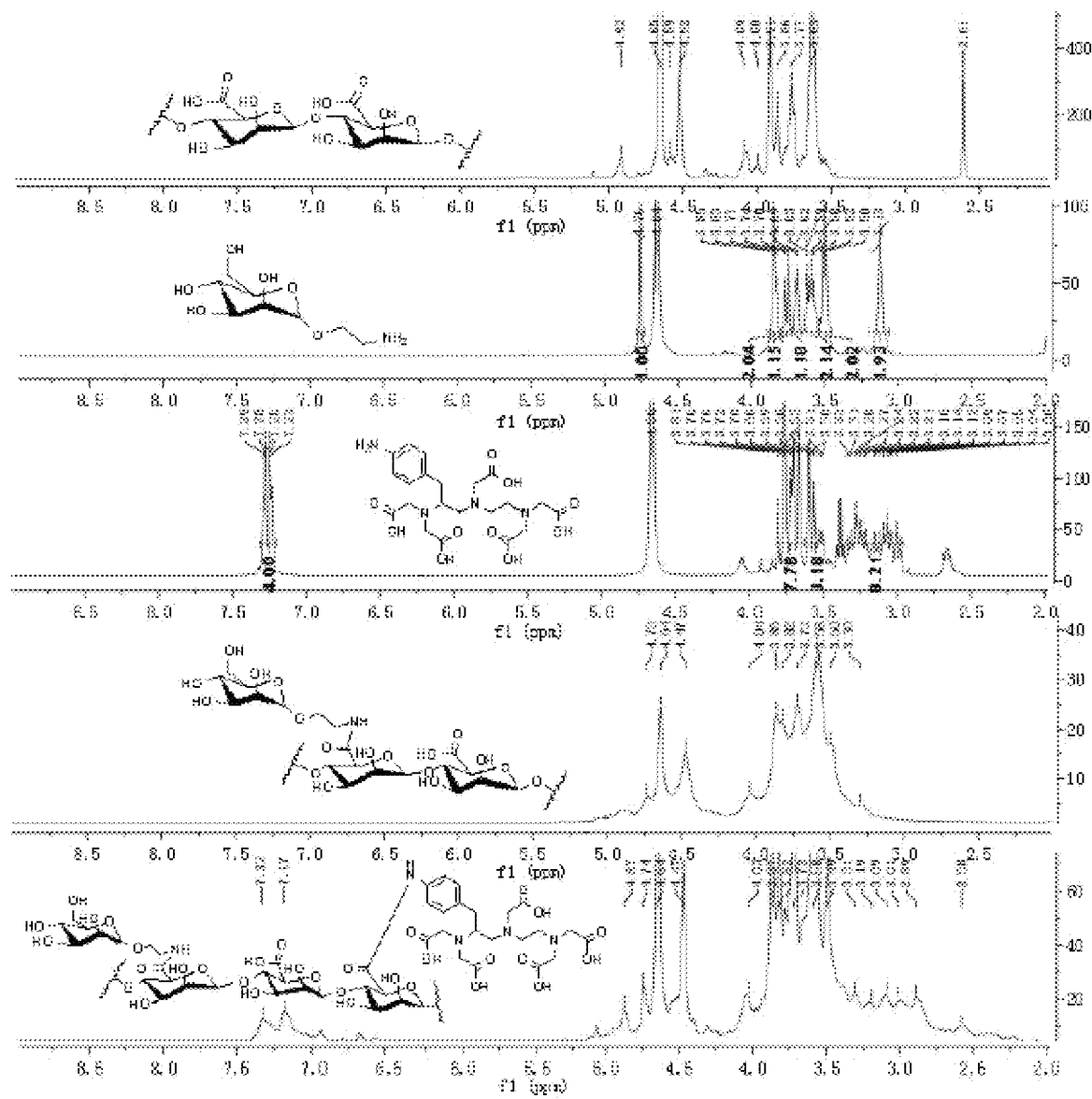
FIG. 6 is a $^1$H NMR spectrum of a compound synthesized in Example 4 of the present invention.
Figure 7:
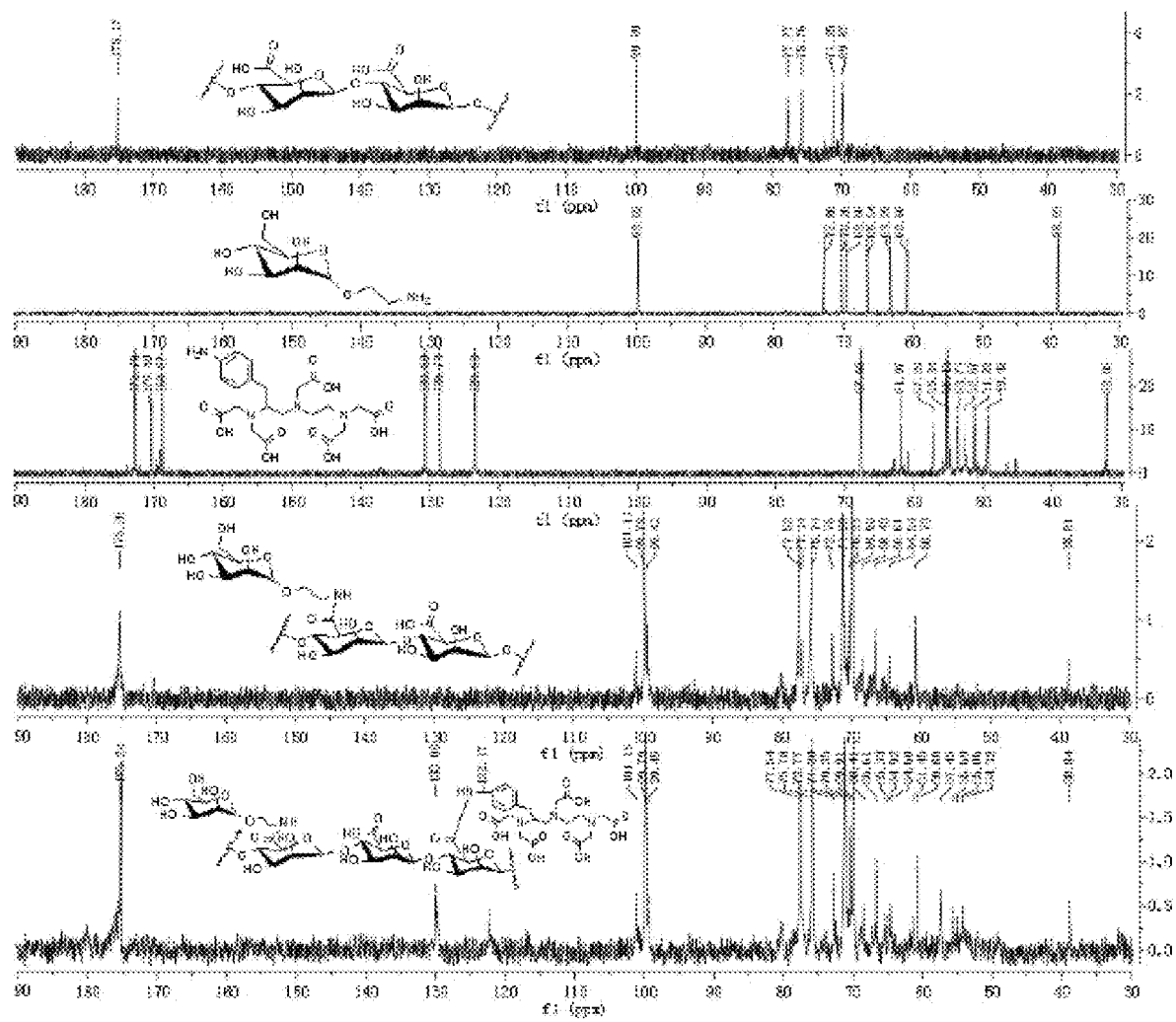
FIG. 7 is a $^{13}$C NMR spectrum of a compound synthesized in Example 4 of the present invention.

The $^1$H NMR spectrum and the $^{13}$C NMR spectrum of the compounds synthesized in Example 4 are shown in FIGS. 6 and 7:

In the $^1$H NMR spectrum of the intermediate PM-M, the sugar ring proton signal and a methylene hydrogen signal on a 1-O-aminoethylmannosyl group coincide with a sugar ring hydrogen signal of PM; only terminal hydrogen signal of δ 4.73 ppm may be found. In the $^1$H NMR spectrum of an intermediate PM-M-NDTPA, δ 7.32, 7.17 ppm is the hydrogen signal of a benzene ring on 1-(p-aminobenzyl)-DTPA; δ 3.31-2.89 ppm is the benzylic position on 1-(p-aminobenzyl)-DTPA and —CH$_2$—NH$_2$ methylene hydrogen signal; —CO—CH$_2$-methylene hydrogen signal coincides with the sugar ring hydrogen signal.

In the $^{13}$C NMR spectrum of the intermediate PM-M, δ 101.11 ppm is the sugar ring terminal carbon signal on the 1-O-aminoethylmannosyl group; δ 99.78, 99.42 ppm are terminal carbon signals of mannuronic acid linked to mannose groups and other mannuronic acids, respectively; δ 70.33, 69.90, 68.40, 66.61, and 64.54 ppm are other carbon signals of the mannose ring; δ 60.79, and 38.81 ppm are connection arm —O—CH$_2$— and —CH$_2$—NH-methylene carbon signals. These new signals indicate that the mannose group is connected to MM. As compared to PM-M, for the $^{13}$C NMR spectrum of the intermediate PM-M-NDTPA, δ 130.00, 122.17 ppm is the carbon signal peak of the benzene ring on 1-(p-aminobenzyl)-DTPA; δ 57.45-54.32 ppm peak is the characteristic peak of —CO—CH$_2$— and —CH$_2$—NH$_2$ methylene carbon on the 1-(p-aminobenzyl)-DTPA.

A healthy New Zealand white rabbit weighing 3.3 kg is provided. The New Zealand white rabbit is intramuscularly anesthetized with ketamine (80 mg/kg, 1.6 ml) and diazepam (5 mg/kg, 1 ml). The rabbit is fixed to a rabbit operating table for MRI scanning. The corresponding parameters are: 3D Fast TOF-SPGRCE-MRA sequence scanning, Flip Angle 30°, TE 1.6 ms, TR 4.5 ms, field of view 280×280 mm, matrix 360×224, layer thickness 1.0 mm, slah70, and NEX 2. Then PM-M-GdNDTPA and HA-DTPA-Gd physiological saline solutions synthesized in Example 4 are subcutaneously injected into the first, the second and the third webbed toes of the left and right hind limbs of the New Zealand rabbit. Each injection is 0.1 ml, gadolinium concentration is 0.03 mmol/ml. After the injection of the contrast agent, scanning is performed every 15-60 min within 5.5 h, a total of scanning is 10 times.

FIG. 12 is a comparative experimental result diagram of a lymph MR imaging of a New Zealand rabbit after the injection of PM-M-GdNDTPA and HA-DTPA-Gd, in the Figure, A: an MR flat scanning image of a lower limb before the injection of the contrast agent; B: an MR image of the lower limb after the injection of the contrast agent for 15 min; C: the MR image of the lower limb after the injection of the contrast agent for 120 min; D: the MR image of the lower limb after the injection of the contrast agent for 4.5 h; R: right side; L: left side.

After the injection of the contrast agent of PM-M-GdNDTPA for 15 min, lymphatic vessels and lymph nodes at both sides are rapidly enhanced; three level-1 lymphatic vessels are clearly developed, and intersected in popliteal lymph nodes; level-2 lymphatic vessels are clearly developed similarly, and extended from the lymph nodes to an abdominal cavity. After the injection of the contrast agent for 120 min, the signal intensities of right lymph nodes and lymphatic vessels injected with HA-DTPA-Gd are significantly weakened while the left lymph nodes and the level-1 and level-2 lymphatic vessels injected with PM-M-GdNDTPA are still maintained at a clear development. After the scanning time is extended to be 4.5 h, the MR image of the left lymph nodes is still distinct and the right lymph nodes are no longer developed.

In a signal enhancement versus time curve (FIG. 13), the left lymph nodes injected with PM-M-GdNDTPA and the right lymph nodes injected with HA-DTPA-Gd have two MR signal enhancement peaks, which are at about 15 min and 120 min, respectively. At 15 min, the MR signal enhancement peak values of the lymph nodes on both sides are about 4, respectively, while at 120 min, the MR signal enhancement peak of the lymph nodes shows a significantly higher signal enhancement ratio in the left lymph nodes than in the right lymph nodes, the peak value of the left side is about 3 times as much as that of the right side. Within 3.5 h thereafter, the signal enhancement rate in the left lymph nodes decreases slowly, and has still a signal enhancement rate of 2.66 at 5.5 h; the right lymph nodes have no enhancement after 4.5 h. This indicates that the contrast agent of PM-M-GdNDTPA of the present invention has excellent developing ability and long lymphatic tissue residence time.

A healthy New Zealand white rabbit weighing 3.34 kg is provided. The New Zealand white rabbit is intramuscularly anesthetized with ketamine (80 mg/kg, 1.6 ml) and diazepam (5 mg/kg, 1 ml). The rabbit is fixed to the rabbit operating table for MRI scanning. The corresponding parameters are: 3D Fast TOF-SPGRCE-MRA sequence scanning, Flip Angle 30°, TE 1.6 ms, TR 4.5 ms, field of view 280×280 mm, matrix 360×224, layer thickness 1.0 mm, slah70, and NEX 2. Then PM-M-GdNDTPA and PM-GdNDTPA physiological saline solutions synthesized in Example 4 are subcutaneously injected into the first, the second and the third webbed toes of the left and right hind limbs of the New Zealand rabbit. Each injection is 0.1 ml, gadolinium concentration is 0.03 mmol/ml. After the injection of the contrast agent, scanning is performed every 15-60 min within 5.5 h, a total of scanning is 10 times.

MR results (FIG. 14) show that the lymphatic vessels and the lymph nodes at both sides are clearly developed after the injection of the contrast agent for 120 min; three level-1 lymphatic vessels go upwards and are intersected in the popliteal lymph nodes, the level-2 lymphatic vessels are clearly developed similarly, and extended from the lymph nodes to the abdominal cavity. The clear contours of the lymph nodes and the level-1 and level-2 lymphatic vessels may be observed on a sagittal plane of a T1-weighted sequence. Compared with PM-GdNDTPA provided in Example 3, PM-M-GdNDTPA provided in Example 4 has better developing effect and longer duration than those of Example 3, it is proved that the introduction of mannose fragments into the contrast agent may significantly increase the lymphatic retention ability of the contrast agent, which is a successful application based on the binding strategy of the mannose receptor.

The signal enhancement versus time curve (FIG. 15) also demonstrates that the mannose fragment increases the ability of the contrast agent to actively target lymphoid tissues. Two MR signal enhancement peaks appear on both sides of the signal enhancement curve, which appear at about 30 min and 120 min, respectively. The signal enhancement rate of the right lymph nodes injected with PM-GdNDTPA is lower than that of the left lymph nodes injected with PM-M-GdNDTPA. The signal enhancement duration of the lymph nodes at both sides is more than 4 h.

Example 5

A carrier is polymannuronic acid (PM); $n_1=12$ $n_2=60$ $n_3=28$; X is a nitrogen atom (N); a linker$_1$ is dimethylene and a linker$_2$ is benzyl; a ligand A is mannose (M) and has the mole content of 12%; a ligand B is a metal chelator 1-(p-aminobenzyl)-DTPA and has the molar content of 60%; a paramagnetic metal is gadolinium (Gd); PM-M-GdNDTPA is obtained. The following reaction processes and steps are provided:

A marine fucoidan polymannuronic acid (PM, 3.52 g, 20 mmol) and an acylation reagent DMT-MM (11.04 g, 40 mmol) are dissolved in deionized water of 50 ml, added with 1-O-aminoethylmannose (1.42 g, 5 mmol) under stirring in batches slowly and stirred and reacted at room temperature for 12 h. After the reaction is completed, a solution is added with $K_2CO_3$ (8.3 g, 60 mmol) and stirred for 0.5 h; the solution is placed in a dialysis bag with a cut-off volume of 3,500 and dialyzed in the deionized water of 5 L, the water is changed every 6 h, a total of water changes is 5 times. After dialysis, the solution is concentrated and lyophilized to obtain a white solid compound PM-M of 3.5 g. The molar ratio of the derivatives of the mannose, an acylation reagents, all carboxyls of the fucoidan is 0.25:1:1.

The intermediate PM-M of 3.5 g and DMT-MM (2.76 g, 10 mmol) prepared in the previous reaction are dissolved in the deionized water of 100 mL, added with 1-(p-aminobenzyl)-DTPA hydrochloride (19.3 g, 30 mmol) under stirring and stirred and reacted at room temperature for 12 h. After the reaction is completed, the solution is added with K2CO3 (8.3 g, 60 mmol) and stirred for 0.5 h. The solution is placed in the dialysis bag with the cut-off volume of 3,500 and dialyzed in the deionized water of 5 L, the water is changed every 6 h, a total of water changes is 5 times. After dialysis, the solution is concentrated and lyophilized to obtain a white solid compound PM-M-NDTPA of 3.1 g. 3 g of PM-M-NDTPA prepared by the reaction is dissolved in the deionized water of 100 ml, and is added with GdCl3.6H$_2$O (9.3 g, 25 mmol) under stirring in batches, the PH of 5% NaOH solution is adjusted to be 5~6. After stirred at room temperature for 1 h, the solution is placed in the dialysis bag with the cut-off volume of 3500 and dialyzed in the deionized water of 5 L, the water is changed every 6 h, a total of water changes is 5 times. After dialysis, the solution is concentrated and lyophilized to obtain a white solid compound PM-M-GdNDTPA of 3.76 g. The molar ratio of the metal chelator, the acylation reagents, metal ions and all carboxyls of the fucoidan is 0.15:0.5:0.125:1.

In the prepared white solid compound PM-M-GdNDTPA, the content of mannose receptor recognition group (a ligand A) is 12%. The content of the paramagnetic metal chelate (a ligand B) is 60%, gadolinium content is 8.32%, the molecular weight thereof is 10.51 kDa.

The contrast test is performed based on the method of Example 4.

FIG. 16 is a comparative experimental result diagram of an lymph MR imaging of a New Zealand rabbit after the injection of PM-M-GdNDTPA and HA-DTPA-Gd in Example 5, in the figure, A: an MR flat scanning image of a lower limb after the injection of the contrast agent for 5 min; B: an MR image of the lower limb after the injection of the contrast agent for 15 min; C: the MR image of the lower hind limb after the injection of the contrast agent for 50 min; R: right side; L: left side.

After the injection of the contrast agent of PM-M-GdNDTPA for 15 min, the signals of the lymphatic vessels and the lymph nodes at both sides are rapidly enhanced, three level-1 lymphatic vessels are clearly developed, and intersected in popliteal lymph nodes; the level-2 lymphatic vessels are clearly developed similarly, and extended from the lymph nodes to an abdominal cavity. After the injection of the contrast agent for 50 min, the signal intensity of the left lymph nodes and the lymphatic vessel injected with HA-DTPA-Gd is significantly weakened, while the right lymph nodes and the level-1 and level-2 lymphatic vessels injected with PM-M-GdNDTPA remain clearly developed.

Example 6

A carrier of a fucoidan is polyguluronic acid (PG); $n_1=40$ $n_2=1$ $n_3=59$; X is a nitrogen atom (N); a linker$_2$ is a benzyl group; a ligand A is mannose (M) and has the molar content of 40%; Ligand B is a metal chelator 1-(p-aminobenzyl)-DTPA with a molar content of 1%; the a paramagnetic metal is gadolinium (Gd); the contrast agent of PG-M-GdNDTPA is obtained. The following reaction processes and steps are provided:

A marine fucoidan polyglucuronic acid (PG, 2.7 g, 15 mmol) and an acylation reagent CDMT (3.51 g, 20 mmol) are dissolved in the deionized water of 50 ml, added with 1-O-aminoethylmannose (4.26 g, 15 mmol) at room temperature under stirring in batches slowly, and stirred and reacted at room temperature under stirring for 12 h. After the reaction is completed, a solution is added with $K_2CO_3$ (8.3 g, 60 mmol) and stirred for 0.5 h; the solution is placed in a dialysis bag with a cut-off volume of 3,500 and dialyzed in the deionized water of 5 L, the water is changed every 6 h, a total of water changes is 5 times. After dialysis, the solution is concentrated and lyophilized to obtain a white solid compound PG-M of 3.1 g. The molar ratio of the derivatives of the mannose, the acylation reagent and all carboxyls of the fucoidan is 0.75:1:0.75.

The intermediate PG-M of 3.1 g and CDMT (1.75 g, 10 mmol) prepared in the previous reaction are dissolved in the deionized water of 100 mL and added with an acid salt (0.019 g, 0.03 mmol) of 1-(p-aminobenzyl)-DTPA and stirred and reacted at room temperature for 12 h. After the reaction is completed, a solution is added with $K_2CO_3$ (8.3 g, 60 mmol) and stirred for 0.5 h. The solution is placed in the dialysis bag with the cut-off volume of 3,500 and dialyzed in the deionized water of 5 L, the water is changed every 6 h, a total of water changes is 5 times. After dialysis, the solution is concentrated and lyophilized to obtain 3.1 g a white solid compound PG-M-NDTPA of 3 g. PG-M-NDTPA prepared by the reaction is dissolved in the deionized water of 100 ml, and added with GdCl3 6H2O (0.93 g, 2.5 mmol) under stirring in batches, the PH of 5% NaOH solution is adjusted to be 5~6. After stirred at room temperature for 1 h, the solution is placed in the dialysis bag with the cut-off volume of 3500 and dialyzed in the deionized water of 5 L, the water is changed every 6 h, a total of water changes is 5 times. After dialysis, the solution was concentrated and lyophilized to obtain a white solid compound PG-M-GdNDTPA of 3.36 g. The molar ratio of a metal chelator, the acylation reagents, metal ions and all carboxyls of the fucoidan is 0.0015:0.5:0.125:1.

In the prepared white solid compound PG-M-GdNDTPA, the content of mannose receptor recognition group (a ligand A) is 40%, the content of paramagnetic metal chelate (a ligand B) is 1%, the content of gadolinium is 6.26%, the molecular weight thereof is 10.48 kDa.

The contrast test is performed based on the method of Example 4.

Next, the development time (h) and the signal enhancement ratio (%) of the macromolecular contrast agent obtained in Embodiments 1-6 and HA-DTPA-Gd (comparative example) with a hyaluronic acid as a carrier disclosed in Patent CN101862461 are compared, specifically:

The macromolecular contrast agent synthesized in Embodiments 1-6 may be clearly developed in both structures of the lymphatic vessels and the lymph nodes after subcutaneous injection, achieving the clear drawing and the precise positioning of the lymph nodes and the lymphatic vessels (Table 5). Compared with the HA-DTPA-Gd with the hyaluronic acid as the carrier disclosed in the patent CN101862461, the signal enhancement rate and the enhancement time of the lymph node, on the side of the animal, which is injected with this type of the contrast agent, are significantly enhanced. At the same time, the contents of PM-GdNDTPA and PM-M-GdNDTPA in the lymph nodes are significantly increased. the high signal enhancement of the lymph nodes (E>2) is maintained for more than 2 h, and PM-GdNDTPA and PM-M-GdNDTPA have also better lymph node resident capacity than contrast agent HA-DTPA-Gd with the hyaluronic acid as the carrier disclosed in Patent CN101862461.B.

TABLE 5

Comparison of contrast agents in the embodiments of the present invention and those of comparative examples

| NO. | Gadolinium concentration (mmol/mL) | Development range | Development time (h) | Signal enhancement rate (%) |
|---|---|---|---|---|
| Example 1 | 0.03 | Level-1 lymphatic vessels, Level-2 lymphatic vessels, lymph nodes | >2 | >3 |
| Example 2 | 0.03 | Level-1 lymphatic vessels, Level-2 lymphatic vessels, lymph nodes | >2 | >3 |
| Example 3 | 0.03 | Level-1 lymphatic vessels, Level-2 lymphatic vessels, lymph nodes | >2 | >3 |

TABLE 5-continued

Comparison of contrast agents in the embodiments of the present invention and those of comparative examples

| NO. | Gadolinium concentration (mmol/mL) | Development range | Development time (h) | Signal enhancement rate (%) |
|---|---|---|---|---|
| Example 4 | 0.03 | Level-1 lymphatic vessels, Level-2 lymphatic vessels, lymph nodes | >5 | >3 |
| Example 5 | 0.03 | Level-1 lymphatic vessels, Level-2 lymphatic vessels, lymph nodes | >5 | >3 |
| Example 6 | 0.03 | Level-1 lymphatic vessels, Level-2 lymphatic vessels, lymph nodes | >2 | >3 |
| Comparative example | 0.03 | Level-1 lymphatic vessels, Level-2 lymphatic vessels, lymph nodes | 1 | 2 |

The macromolecular MR contrast agent with the fucoidan as the carrier according to the present invention shows significant difference in lymph retention level, which may be due to the different recognition and binding force of the mannose receptor (MBP) in the lymphoid tissue on polymannuronic acid (PM) and mannose ligand. This result is in line with the original design of this thesis based on MBP combined strategy to synthesize an active targeted contrast agent. In summary, the MRI contrast agent prepared by the invention has stronger lymphoid tissue resident ability and longer time, clearer lymphatic tissue development, and has great clinical application potential for examination and diagnosis of lymphatic system diseases.

The invention claimed is:

1. A lymph targeted magnetic resonance contrast agent with a fucoidan as a carrier, wherein the contrast agent has the following structure: the fucoidan is used as a carrier, and a 6-position carboxyl thereof is combined with a mannose receptor MBP recognition group ligand A and a paramagnetic metal chelate ligand B, the contrast agent has the following general formula:

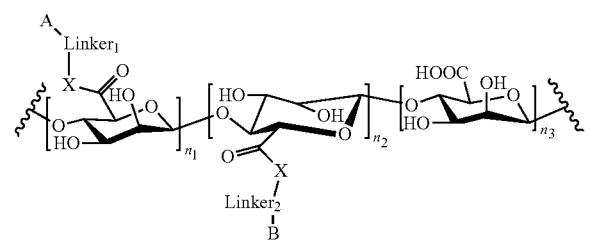

wherein: $n_1$ is an integer, each of $n_2$ and $n_3$ is a positive integer; X is NH; the ligand A is a mannose receptor MBP recognition group; and the ligand B is a paramagnetic metal chelate and the paramagnetic metal chelate ligand B contains a paramagnetic metal ion, and the structure of X-linker$_2$-ligand B without the paramagnetic metal ion is as follows:

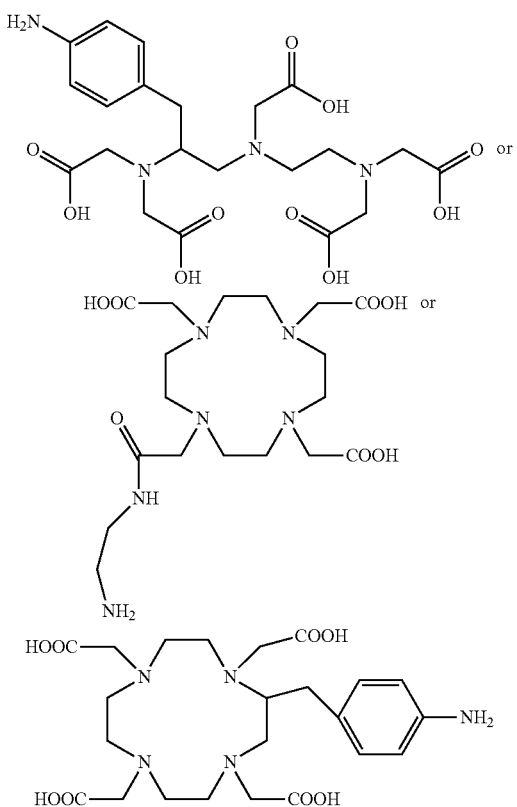

and "X-Linker2" in the general formula is

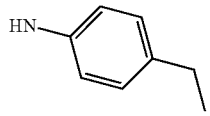

or "NH-CH2-CH2-", and "X-Linker1" in the general formula is "NH-CH2-CH2-";

wherein the molar content of the ligand A accounts for 0-40% of the original carboxyl of the fucoidan, the molar content of the ligand B accounts for 1-60% of the original carboxyl of the fucoidan, wherein the total of the molar content of ligand A, the molar content of ligand B and the molar content of unreacted carboxyl in the original carboxyl of the fucoidan is 100%.

2. The lymph targeted magnetic resonance contrast agent according to claim 1, wherein the molar content of the ligand A accounts for 15% to 40% of the original carboxyl of the fucoidan, the molar content of the ligand B accounts for 16% to 60% of the original carboxyl of the fucoidan, wherein the total of the molar content of ligand A, the molar content of ligand B and the molar content of unreacted carboxyl in the original carboxyl of the fucoidan is 100%.

3. The lymph targeted magnetic resonance contrast agent according to claim 1, wherein the carrier of the fucoidan is polymannuronic acid PM or polyguluronic acid PG and includes the corresponding carboxylate salt form thereof, and has a molecular weight of 100-$10^8$ Da.

4. The lymph targeted magnetic resonance contrast agent according to claim 1, the paramagnetic metal ions used are divalent ions or trivalent ions of Gd, Mn, Cr, Fe, Co, Ni, La, Tc, Dy or Cu.

5. The lymph targeted magnetic resonance contrast agent according to claim 1, wherein n1 is 12-40, n2 is 1-60, and n1+n2+n3=100.

6. The lymph targeted magnetic resonance contrast agent according to claim 5, wherein n1 is 15-40, n2 is 15-60, and n1+n2+n3=100.

7. The lymph targeted magnetic resonance contrast agent according to claim 1, wherein the molar content of the ligand A is 12-15%.

8. The lymph targeted magnetic resonance contrast agent according to claim 1, wherein the molar content of the ligand A is 15-40%.

9. The lymph targeted magnetic resonance contrast agent according to claim 5, the linker$_1$ is —CH$_2$—CH$_2$—, and the linker$_2$ is benzyl.

10. The lymph targeted magnetic resonance contrast agent according to claim 1, wherein n1 is 15-40, n2 is 15-60, and n1+n2+n3=100; and the linker$_1$ is —CH$_2$—CH$_2$—, and the linker$_2$ is benzyl.

11. The lymph targeted magnetic resonance contrast agent according to claim 1, wherein n1 is 20, n2 is 15, and n3=65; the linker$_1$ is —CH$_2$—CH$_2$—; and the linker$_2$ is benzyl.

12. The lymph targeted magnetic resonance contrast agent of claim 1, wherein the structure of the lymph targeted magnetic resonance contrast agent is shown as below:

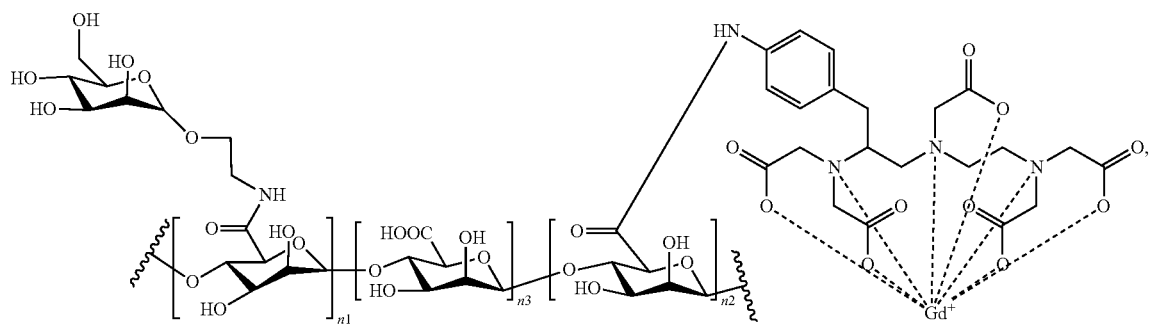

wherein n1 is 12-40, n2 is 1-60, and n1+n2+n3=100.

* * * * *